US011023592B2

(12) United States Patent
Sher-Jan et al.

(10) Patent No.: US 11,023,592 B2
(45) Date of Patent: *Jun. 1, 2021

(54) SYSTEMS AND METHODS FOR MANAGING DATA INCIDENTS

(71) Applicant: RADAR, LLC, Portland, OR (US)

(72) Inventors: Mahmood Sher-Jan, Lake Oswego, OR (US); Andrew Migliore, Portland, OR (US); Nicholas J. Church, Milwaukie, OR (US); Reno Brown, Portland, OR (US); David Van Der Merwe, Portland, OR (US)

(73) Assignee: RADAR, LLC, Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/559,513

(22) Filed: Sep. 3, 2019

(65) Prior Publication Data
US 2019/0392154 A1 Dec. 26, 2019

Related U.S. Application Data

(63) Continuation of application No. 16/235,872, filed on Dec. 28, 2019, now Pat. No. 10,445,508, which is a
(Continued)

(51) Int. Cl.
*G06F 21/60* (2013.01)
*G06F 21/00* (2013.01)
(Continued)

(52) U.S. Cl.
CPC .............. *G06F 21/60* (2013.01); *G06F 21/00* (2013.01); *G06F 21/554* (2013.01);
(Continued)

(58) Field of Classification Search
CPC ........ G06F 21/60; G06F 21/00; G06F 21/554; G06F 21/577; G06F 21/6245;
(Continued)

(56) References Cited

U.S. PATENT DOCUMENTS 6,148,297 A 11/2000 Swor et al.
6,324,647 B1 11/2001 Bowman-Amuah
(Continued)

OTHER PUBLICATIONS

European Commission, "Proposal for a Regulation of the European Parliament and of the Council on the Protection of Individuals with Regard to the Processing of Personal Data and on the Free Movement of Such Data (General Data Protection Regulation)", European Commission, Brussels, COM(2012) 11 final, 2012/0011 (COD), Jan. 25, 2012, 119 pages.

*Primary Examiner* — Shahriar Zarrineh
(74) *Attorney, Agent, or Firm* — Carr & Ferrell LLP

(57) ABSTRACT

Systems and methods for managing a multi-region data incident are provided herein. Example methods include receiving, via a risk assessment server, in response to an occurrence of the data incident, data incident data that including information corresponding to the data incident, wherein the data incident has a plurality of facets with each facet having any of unique and overlapping set of privacy data and media type and associated risk factors requiring facet specific incident risk assessment, automatically generating, via the risk assessment server, a risk assessment and decision-support guidance whether the facet is reportable, from a comparison of the facet to privacy rules, the privacy rules define requirements associated with data incident notification obligations, and providing, via the risk assessment server, the risk assessment to a display device that selectively couples with the risk assessment server.

20 Claims, 42 Drawing Sheets

Related U.S. Application Data continuation-in-part of application No. 15/786,538, filed on Oct. 17, 2017, now Pat. No. 10,331,904, which is a continuation-in-part of application No. 15/339,786, filed on Oct. 31, 2016, now Pat. No. 10,204,238, which is a continuation-in-part of application No. 14/868,311, filed on Sep. 28, 2015, now Pat. No. 9,781,147, which is a continuation-in-part of application No. 14/588,159, filed on Dec. 31, 2014, now Pat. No. 9,483,650, which is a continuation-in-part of application No. 14/311,253, filed on Jun. 21, 2014, now abandoned, which is a continuation of application No. 13/691,661, filed on Nov. 30, 2012, now Pat. No. 8,763,133, which is a continuation of application No. 13/396,558, filed on Feb. 14, 2012, now Pat. No. 8,707,445.

(51) Int. Cl.
| | |
|---|---|
| G06F 21/62 | (2013.01) |
| G06F 21/57 | (2013.01) |
| H04L 29/06 | (2006.01) |
| G16H 10/60 | (2018.01) |
| G06F 21/55 | (2013.01) |
| H04W 12/02 | (2009.01) |

(52) U.S. Cl.
CPC ........ G06F 21/577 (2013.01); G06F 21/6245 (2013.01); G16H 10/60 (2018.01); H04L 63/0227 (2013.01); H04L 63/1433 (2013.01); H04W 12/02 (2013.01); H04L 63/0407 (2013.01); H04L 63/08 (2013.01); H04L 63/1408 (2013.01); H04L 63/1416 (2013.01)

(58) Field of Classification Search
CPC . G16H 10/60; H04L 63/0227; H04L 63/1433; H04L 63/0407; H04L 63/08; H04L 63/1408; H04L 63/1416; H04W 12/02; G06Q 10/0635
See application file for complete search history.

(56) References Cited

U.S. PATENT DOCUMENTS

| | | | |
|---|---|---|---|
| 6,901,372 | B1 | 5/2005 | Helzerman |
| 6,925,443 | B1 | 8/2005 | Baggett, Jr. et al. |
| 6,985,922 | B1 | 1/2006 | Bashen et al. |
| 7,287,008 | B1 | 10/2007 | Mahoney et al. |
| 7,343,303 | B2 | 3/2008 | Meyer et al. |
| 7,657,942 | B2 | 2/2010 | Himberger et al. |
| 7,676,426 | B2 | 3/2010 | Lawrence et al. |
| 7,739,132 | B2 | 6/2010 | Denny, Jr. et al. |
| 7,813,944 | B1 | 10/2010 | Luk et al. |
| 7,873,660 | B1 | 1/2011 | Wong et al. |
| 7,996,374 | B1 | 8/2011 | Jones et al. |
| 8,020,210 | B2 | 9/2011 | Tippett et al. |
| 8,185,931 | B1 | 5/2012 | Reeves |
| 8,332,959 | B2 | 12/2012 | Chen et al. |
| 8,380,841 | B2 | 2/2013 | Dunagan et al. |
| 8,407,194 | B1 | 3/2013 | Chaput et al. |
| 8,468,244 | B2 | 6/2013 | Redlich et al. |
| 8,607,353 | B2* | 12/2013 | Rippert, Jr. ............ G06Q 10/10 726/25 |
| 8,650,067 | B1 | 2/2014 | Moss |
| 8,683,052 | B1 | 3/2014 | Brinskelle |
| 8,707,445 | B2 | 4/2014 | Sher-Jan et al. |
| 8,744,894 | B2* | 6/2014 | Christiansen ........ G06Q 10/06 705/7.28 |
| 8,763,133 | B2 | 6/2014 | Sher-Jan et al. |
| 9,032,531 | B1* | 5/2015 | Scorvo ................ H04L 63/1408 726/25 |
| 9,443,085 | B2* | 9/2016 | Glew .................... G06F 21/577 |
| 9,483,650 | B2 | 11/2016 | Sher-Jan et al. |
| 9,781,147 | B2 | 10/2017 | Sher-Jan et al. |
| 10,204,238 | B2 | 2/2019 | Sher-Jan et al. |
| 10,331,904 | B2 | 6/2019 | Sher-Jan et al. |
| 10,445,508 | B2 | 10/2019 | Sher-Jan et al. |
| 2002/0010784 | A1* | 1/2002 | Clayton ............... G06F 21/6245 709/229 |
| 2002/0029157 | A1 | 3/2002 | Marchosky |
| 2002/0091549 | A1 | 7/2002 | Provost et al. |
| 2002/0111833 | A1 | 8/2002 | Dick |
| 2002/0116247 | A1 | 8/2002 | Tucker et al. |
| 2002/0120477 | A1 | 8/2002 | Jinnett |
| 2003/0056116 | A1 | 3/2003 | Bunker et al. |
| 2003/0074250 | A1 | 4/2003 | Burk |
| 2003/0093365 | A1 | 5/2003 | Halper et al. |
| 2003/0135397 | A1 | 6/2003 | Halow et al. |
| 2003/0149598 | A1* | 8/2003 | Santoso ................. G16H 50/20 705/2 |
| 2003/0217037 | A1 | 11/2003 | Bicker et al. |
| 2003/0225690 | A1 | 12/2003 | Eaton |
| 2004/0073445 | A1* | 4/2004 | Mellinger .......... G06Q 30/0282 726/25 |
| 2004/0098285 | A1 | 5/2004 | Breslin et al. |
| 2004/0102923 | A1* | 5/2004 | Tracy ..................... G06Q 10/10 702/181 |
| 2004/0128186 | A1* | 7/2004 | Breslin ............ G06Q 10/06311 705/7.13 |
| 2004/0128543 | A1 | 7/2004 | Blake et al. |
| 2004/0193870 | A1 | 9/2004 | Redlich et al. |
| 2004/0193907 | A1 | 9/2004 | Patanella |
| 2005/0044357 | A1 | 2/2005 | Fano |
| 2005/0066195 | A1 | 3/2005 | Jones |
| 2005/0132225 | A1 | 6/2005 | Gearhart |
| 2005/0141941 | A1 | 6/2005 | Narusawa et al. |
| 2005/0171941 | A1 | 8/2005 | Chen et al. |
| 2005/0193430 | A1 | 9/2005 | Cohen et al. |
| 2005/0203775 | A1* | 9/2005 | Chesbrough ........... G16H 80/00 705/2 |
| 2005/0273360 | A1 | 12/2005 | Drucker et al. |
| 2006/0020495 | A1 | 1/2006 | Baker et al. |
| 2006/0026042 | A1 | 2/2006 | Awaraji et al. |
| 2006/0075503 | A1 | 4/2006 | Bunker et al. |
| 2006/0089861 | A1* | 4/2006 | King ...................... G06Q 10/06 705/4 |
| 2006/0101508 | A1 | 5/2006 | Taylor |
| 2006/0190986 | A1 | 8/2006 | Mont et al. |
| 2006/0247947 | A1 | 11/2006 | Suringa |
| 2006/0277071 | A1 | 12/2006 | Shufeldt |
| 2006/0282291 | A1 | 12/2006 | Runciman |
| 2006/0287953 | A1 | 12/2006 | Chauhan |
| 2007/0016954 | A1 | 1/2007 | Choi et al. |
| 2007/0038484 | A1 | 2/2007 | Hoffner et al. |
| 2007/0067845 | A1* | 3/2007 | Wiemer ............... H04L 63/1433 726/25 |
| 2007/0078668 | A1 | 4/2007 | Pathria et al. |
| 2007/0136814 | A1 | 6/2007 | Lee et al. |
| 2007/0250377 | A1 | 10/2007 | Hill, Jr. et al. |
| 2007/0282796 | A1 | 12/2007 | Evenhaim |
| 2008/0015978 | A1 | 1/2008 | Curry et al. |
| 2008/0047016 | A1 | 2/2008 | Spoonamore |
| 2008/0059230 | A1 | 3/2008 | Manning et al. |
| 2008/0086342 | A1 | 4/2008 | Curry et al. |
| 2008/0133300 | A1* | 6/2008 | Jalinous .............. G06Q 10/0635 705/7.28 |
| 2008/0133531 | A1 | 6/2008 | Baskerville et al. |
| 2008/0147441 | A1 | 6/2008 | Kil |
| 2008/0162496 | A1 | 7/2008 | Postrel |
| 2008/0177760 | A1 | 7/2008 | Fein |
| 2009/0024663 | A1 | 1/2009 | McGovern |
| 2009/0043637 | A1* | 2/2009 | Eder ....................... G06N 7/005 705/35 |
| 2009/0070434 | A1 | 3/2009 | Himmelstein |
| 2009/0119141 | A1* | 5/2009 | McCalmont ........ G06Q 10/0639 705/7.41 |
| 2009/0210256 | A1 | 8/2009 | Upadhyayula et al. |
| 2009/0313049 | A1 | 12/2009 | Joao et al. |
| 2009/0319420 | A1 | 12/2009 | Sanchez et al. |
| 2010/0004956 | A1 | 1/2010 | McCallum et al. |

(56) References Cited

U.S. PATENT DOCUMENTS

| | | |
|---|---|---|
| 2010/0017870 A1 | 1/2010 | Kargupta |
| 2010/0042440 A1 | 2/2010 | Joao |
| 2010/0114607 A1 | 5/2010 | Kress et al. |
| 2010/0114634 A1* | 5/2010 | Christiansen ........ G06Q 30/018 705/7.28 |
| 2010/0185500 A1* | 7/2010 | Estrella ............. G06Q 10/1057 705/7.28 |
| 2010/0199338 A1 | 8/2010 | Craddock et al. |
| 2010/0205014 A1* | 8/2010 | Sholer .................... G06Q 10/00 705/4 |
| 2010/0262668 A1 | 10/2010 | Piett et al. |
| 2010/0275263 A1 | 10/2010 | Bennett et al. |
| 2011/0016377 A1* | 1/2011 | Caldwell ............... G06Q 10/10 715/205 |
| 2011/0066562 A1* | 3/2011 | Stapleton ............... G06Q 10/00 705/317 |
| 2011/0126111 A1 | 5/2011 | Gill et al. |
| 2011/0134473 A1 | 6/2011 | Sato |
| 2011/0289588 A1 | 11/2011 | Sahai et al. |
| 2012/0030767 A1 | 2/2012 | Rippert, Jr. et al. |
| 2012/0072991 A1 | 3/2012 | Belani et al. |
| 2012/0143650 A1 | 6/2012 | Crowley |
| 2012/0180133 A1 | 7/2012 | Al-Harbi |
| 2012/0331567 A1 | 12/2012 | Shelton |
| 2013/0055337 A1 | 2/2013 | Choi et al. |
| 2013/0124223 A1 | 5/2013 | Gregg |
| 2013/0212683 A1 | 8/2013 | Sher-Jan et al. |
| 2013/0212692 A1 | 8/2013 | Sher-Jan et al. |
| 2014/0089039 A1* | 3/2014 | McClellan ......... G06Q 10/0635 705/7.28 |
| 2014/0101774 A1 | 4/2014 | Armington et al. |
| 2014/0259095 A1 | 9/2014 | Bryant |
| 2014/0259170 A1 | 9/2014 | Amsler |
| 2014/0304822 A1 | 10/2014 | Sher-Jan et al. |
| 2015/0113663 A1 | 4/2015 | Sher-Jan et al. |
| 2016/0021133 A1 | 1/2016 | Sher-Jan et al. |
| 2017/0206376 A1 | 7/2017 | Sher-Jan |
| 2017/0270318 A1 | 9/2017 | Ritchie |
| 2017/0286717 A1 | 10/2017 | Khi et al. |
| 2018/0039794 A1 | 2/2018 | Sher-Jan |
| 2018/0137305 A1 | 5/2018 | Barday |
| 2019/0138734 A1 | 5/2019 | Sher-Jan et al. |

* cited by examiner

CALIFORNIA CIVIL CODE:

Privacy Law (s): California Civil Code 1798.29 & 1798.82 (SB 1386 & SB24)

Application: Any agency, person, or business that conducts business in California and that owns or licenses computerized data that includes personal information on California residents.

Breach Definition: Unauthorized acquisition of computerized data that compromises the security, confidentiality, or integrity of personal information maintained by the agency.

Harm Test: No, California Civil Code does not provide for a harm test as a condition of notification decision.

Allowed Exception (s): Yes, the California Civil Code provides for exception(s) from notification obligation. RADAR will automatically flag if/when an exception is applicable to the incident based on the user's documentation of each incident's unique profile information. The user is advised to further assess the applicability of the exception prior to making notification decision.

CALIFORNIA HEALTH AND SAFETY CODE:

Privacy Law (s): California Health & Safety Code (1280.15)

Application: A clinic, health facility, home health agency, or hospice licensed by California Department of Public Health (CDPH) pursuant to Section 1204, 1250, 1725, or 1745.

Breach Definition: Unlawful or unauthorized access to, and use or disclosure of, patients' medical information, as defined in subdivision (g) of Section 56.05 of the Civil Code and consistent with Section 130203

Harm Test: No, California Health & Safety Code does not provide for a harm test as a condition of notification decision.

Allowed Exception(s): Yes, the California Health & Safety Code provides for exception(s) from notification obligation. RADAR will automatically flag if/when an exception is applicable to the incident based on the user's documentation of each incident's unique profile information. The user is advised to further assess the applicability of the exception prior to making notification decision.

FIG. 9

| RADAR Client Types | RADAR Client's role | Internal – Notifications | External |
|---|---|---|---|
| Healthcare Provider | CE | Patients & Gov't agencies | Patients & Gov't agencies |
| Healthcare Provider | BA | Affected CEs by the breach. | CEs affected by the breach. |
| Healthcare Provider | CE & BA | Patients & Gov't agencies as CE & Affected CEs as BA | Patients & Gov't agencies & CEs affected by the breach. |
| Health Plan | CE: (Individual plans & Fully Insured Group Plans) | Members/Individuals & Gov't agencies | Members/Individuals & Gov't agencies unless delegated per BAA |
| Health Plan | BA: TPA (for Self-Insured Health Plan) | Affected Self-Insured Health Plan Sponsors/Employers; Members/employees only per BAA | Affected Self-Insured Plan Sponsors/Employers as CE; |
| Health Plan | CE & BA (If a plan breaches data belonging to its members and its plan sponsors' members) | Members & Gov't agencies as CE & Affected Plan Sponsors as BA | Affected Self-Insured Plan Sponsors/Employers as BA. |
| Self-Insured Health Plan / Health Plan Sponsor (Employer/Union) | CE | Employees & Gov't agencies unless delegated to Health Plan per BAA | Employees & Gov't agencies unless delegated to Health Plan per BAA |

| State | Thumbdrive | Tablet | Statements | Total | AG notification (threshold) |
|---|---|---|---|---|---|
| CA | 400 | 100 | 200 | 700 | No (500) |
| HI | 600 | 100 | 500 | 1200 | No (1000) |
| OR | 100 | 200 | 100 | 350 | No (250) |

*Table 1*

*FIG. 36*

| One region, no facets | One region, facets | Multiple regions, no facets | Multiple regions, facets |
|---|---|---|---|
| Basics<br>• Name<br>• Document only<br>• Occurred<br>• Occurrence location<br>• First informed<br>• Discovered / Aware<br>• Discovery method<br>• Estimated individuals<br>• Reported employees | Basics<br>• Name<br>• Document only<br>• Occurred<br>• Occurrence location<br>• First informed<br>• Discovered / Aware<br>• Discovery method<br>• Estimated individuals | Basics<br>• Name<br>• Document only<br>• Occurred<br>• Occurrence location<br>• First informed<br>• Discovered / Aware<br>• Discovery method<br>• Estimated individuals | Basics<br>• Name<br>• Document only<br>• Occurred<br>• Occurrence location<br>• First informed<br>• Discovered / Aware<br>• Discovery method<br>• Estimated individuals |
| Description | Description | Description | Description |
| Reporter<br>• First name<br>• Last name<br>• Phone<br>• Email | Reporter<br>• First name<br>• Last name<br>• Phone<br>• Email | Reporter<br>• First name<br>• Last name<br>• Phone<br>• Email | Reporter<br>• First name<br>• Last name<br>• Phone<br>• Email |
| Organizational context<br>• Incident group<br>• Department<br>• Source<br>• Employee involved<br>• External entity involved<br>• Date notified by EE | Organizational context<br>• Incident group<br>• Department<br>• Source<br>• Employee involved<br>• External entity involved<br>• Date notified by EE | Organizational context<br>• Incident group<br>• Department<br>• Source<br>• Employee involved<br>• External entity involved<br>• Date notified by EE | Organizational context<br>• Incident group<br>• Department<br>• Source<br>• Employee involved<br>• External entity involved<br>• Date notified by EE |
| Individuals impacted<br>• Number impacted | | | |
| Data context<br>• Your organization's role | Data context<br>• Your organization's role | Data context<br>• Your organization's role | Data context<br>• Your organization's role |
| Risk factors | Risk factors | Risk factors | Risk factors |
| Data elements<br>• Contextual sensitivity | Data elements<br>• Contextual sensitivity | Data elements<br>• Contextual sensitivity | Data elements<br>• Contextual sensitivity |
| Jurisdictions | Jurisdictions | Jurisdictions | Jurisdictions |

3900 — One region, no facets
3902 — One region, facets
3904 — Multiple regions, no facets
3906 — Multiple regions, facets Legend:
* Bold text indicates data added to the Profile page via the webform.
* Red text indicates fields that are facetized.
* Blue text indicates fields that are regionalized.

SYSTEMS AND METHODS FOR MANAGING DATA INCIDENTS

CROSS-REFERENCE TO RELATED APPLICATIONS

The present continuation application claims the priority benefit of U.S. Non-Provisional patent application Ser. No. 16/235,872 filed on Dec. 28, 2018, now U.S. Pat. No. 10,455,508, issued on Oct. 15, 2019, which is a continuation-in-part that claims the benefit and priority of U.S. Non-Provisional patent application Ser. No. 15/786,538 filed on Oct. 17, 2017, now U.S. Pat. No. 10,331,904, issued on Jun. 25, 2019, which is a continuation-in-part that claims the benefit and priority of U.S. Non-Provisional patent application Ser. No. 15/339,786 filed on Oct. 31, 2016, now U.S. Pat. No. 10,204,238, issued on Feb. 12, 2019, which is a continuation-in-part that claims the benefit and priority of U.S. Non-Provisional patent application Ser. No. 14/868,311 filed on Sep. 28, 2015, now U.S. Pat. No. 9,781,147, issued on Oct. 3, 2017, which is a continuation-in-part that claims the benefit and priority of U.S. Non-Provisional patent application Ser. No. 14/588,159 filed on Dec. 31, 2014, now U.S. Pat. No. 9,483,650, issued on Nov. 1, 2016, which is a continuation-in-part and claims the benefit and priority of U.S. Non-Provisional patent application Ser. No. 14/311,253 filed on Jun. 21, 2014, which is a continuation that claims the benefit and priority of U.S. Non-Provisional patent application Ser. No. 13/691,661 filed on Nov. 30, 2012, now U.S. Pat. No. 8,763,133, issued on Jun. 24, 2014, which is a continuation that claims the benefit and priority of U.S. Non-Provisional patent application Ser. No. 13/396,558 filed on Feb. 14, 2012, now U.S. Pat. No. 8,707,445, issued on Apr. 22, 2014, all of which are hereby incorporated by reference herein in their entirety including all references cited therein.

FIELD OF THE TECHNOLOGY

Embodiments of the disclosure relate to information privacy. More specifically, but not by way of limitation, the present technology relates to the management of multi-region data incidents. Multi-region data incidents may involve a breach of privacy that cross many overlapping and/or non-overlapping data types, risks, individuals, rules, and so forth. These rules can include aspects of local, state, federal, international, contractual, and other similar laws or obligations.

The management of a multi-region data incident may comprise conducting an analysis of a data incident data relative to privacy rules and generating a risk assessment and incident response plan for the multi-region data incident. Additionally, the present technology may generate notification schedules and gather/transmit notification information for multi-region data incidents having a risk assessment that is indicative of any level of risk.

BACKGROUND OF THE DISCLOSURE

Data incidents involve the exposure of sensitive information such as personally identifiable information and protected health information to third parties. Data incidents may comprise data breaches, privacy breaches, privacy or security incidents, and other similar events that result in the exposure of sensitive information to third parties. Some of these exposures may be subject to numerous United States (US) state and federal statutes and international laws that delineate requirements that are to be imposed upon the party that was entrusted to protect the data. Personally identifiable information (hereinafter "PII") and protected health information (PHI) which, regards healthcare related information for individuals that are maintained by a covered entity (e.g., an entity that has been entrusted with the PHI such as a hospital, clinic, health plan, and so forth), may include, but is not limited to, healthcare, financial, political, reputational, criminal justice, biological, location, and/or ethnicity information. For purposes of brevity, although each of these types of PII and PHI may have distinct nomenclature, all the aforementioned types of information will be referred to herein as PII/PHI. PII/PHI are definitions typically under US laws. Various embodiments of the present technology include systems and methods for managing multi-region data incidents that involve "Personal Data," which comprises any information about an individual that is considered protected under data privacy and protection laws, including but not limited to PII/PHI. In some embodiments, contractual privacy obligations may exist between, for example, an employee and employer or between an employee or contractor and a government agency. These private contracts can also include breach mitigation or notification obligations, which can be risk assessed with the systems and methods disclosed herein.

SUMMARY OF THE DISCLOSURE

According to some embodiments the present technology may be directed to a method for managing a multi-region data incident under privacy laws of at least two regions, comprising: (a) receiving, via a risk assessment server, in response to an occurrence of a multi-region data incident, multi-region data incident data comprising information corresponding to the multi-region data incident, the multi-region data incident comprising intentional or unintentional compromise, disclosure or release of personal data or personally identifiable information to an untrusted or unauthorized environment in violation of privacy laws of at least two regions, the multi-region data incident having a plurality of facets with each facet comprising any of unique and overlapping set of privacy data and media type and associated risk factors requiring facet specific incident risk assessment; (b) displaying, using the risk assessment server, applicable jurisdictions based on the multi-region data incident data; (c) displaying, using the risk assessment server, plurality of applicable privacy rules based on the applicable jurisdictions; (d) automatically generating, using the risk assessment server, a risk assessment and decision-support guidance whether the facet is reportable from a comparison of each of the plurality of applicable privacy rules; wherein the applicable privacy rules define requirements associated with multi-region data incident notification obligations of the privacy laws of the at least two regions, the applicable privacy rules being dependent on an applicable facet of the plurality of facets; and (e) providing, via the risk assessment server, the risk assessment and the decision-support guidance to a display device that selectively couples with the risk assessment server.

According to some embodiments the risk assessment comprises a determination as to whether a number of unique or non-unique but overlapping individuals across the plurality of facets meet notification thresholds based on the applicable jurisdictions.

According to various embodiments each data incident comprises any of risk factors, the multi-region data incident data, and a plurality of jurisdictions.

According to some embodiments the applicable jurisdictions comprises at least two jurisdictions of United States, European Union, Canada, Asia, Middle East, Africa, and South America regions.

According to various embodiments one or more of the plurality of facets is associated with a collection of privacy data determined by a regulatory agency in one or more of the applicable jurisdictions.

According to some embodiments one or more of the plurality of facets is capable of being assessed independently of other ones of the plurality of facets. According to various embodiments each of the plurality of facets comprises a complete set of privacy data.

According to some embodiments the receiving of the multi-region data incident data comprises: providing one or more multi-region data incident risk factor questions to the display device that elicit information corresponding to each of the plurality of facets the multi-region data incident; receiving responses to the one or more of the multi-region data incident risk factor questions; providing the responses to the display device; and receiving confirmation of at least a portion of the responses.

According to various embodiments the plurality of applicable privacy rules comprise privacy rules from a plurality of applicable jurisdictions.

According to some embodiments the risk assessment comprises a risk level that indicates severity of the multi-region data incident relative to the plurality of applicable privacy rules; and wherein the risk level is associated with a color, wherein a hue of the color is associated with the severity of the multi-region data incident and a sensitivity of the data incident data as determined by the comparison.

According to various embodiments the risk assessment defines one or more exceptions that apply to at least a portion of the multi-region data incident data based upon the comparison.

According to some embodiments the method further comprises generating a notification schedule when the comparison indicates that the multi-region data incident violates and triggers a notification obligation according to a plurality of applicable jurisdictions.

According to various embodiments the method further comprises providing an alert to the display device when the comparison indicates that one or more of the plurality of facets of the multi-region data incident violates and triggers a notification obligation according to the privacy rules, further wherein the notification schedule comprises notification dates that are based upon a violated one of the privacy rules, along with notification requirements that describe information that is to be provided to a regulatory agency or to an affected individual whose personal data has been compromised, disclosed or released as a result of the multi-region data incident.

According to various embodiments the method receiving the information that is to be provided to a regulatory agency or to an affected individual and storing the information in a content repository associated with the risk assessment server.

According to various embodiments the comparison includes modeling of the multi-region data incident data to the plurality of applicable privacy rules to determine a severity and a data sensitivity of the multi-region data incident.

According to various embodiments the comparing comprises: modeling the multi-region data incident data to determine severity and data sensitivity of the multi-region data incident by evaluating the multi-region data incident data relative to the plurality of applicable privacy rules; and generating a risk assessment from the modeling of the multi-region data incident data.

According to some embodiments the present technology may be directed to a risk assessment server for managing a multi-region data incident under privacy laws of at least two regions, the server comprising: (a) a memory for storing executable instructions; (b) a processor for executing the instructions; (c) an input module stored in memory and executable by the processor to receive in response to an occurrence of the multi-region data incident, multi-region data incident data comprising information corresponding to the multi-region data incident, the multi-region data incident comprising intentional or unintentional compromise, disclosure or release of personal data or personally identifiable information to an untrusted or unauthorized environment in violation of privacy laws of at least two regions, the multi-region data incident having a plurality of facets with each facet comprising any of unique and overlapping set of privacy data and media type and associated risk factors requiring facet specific incident risk assessment; (d) a risk assessment generator stored in memory and executable by the processor to display applicable jurisdictions based on the multi-region data incident data; display a plurality of applicable privacy rules based on the applicable jurisdictions; and automatically generate a risk assessment and decision-support guidance whether the facet is reportable from a comparison of each of the plurality of applicable privacy rules; wherein the applicable privacy rules define requirements associated with multi-region data incident notification obligations of the privacy laws of the at least two regions, the applicable privacy rules being dependent on an applicable facet of the plurality of facets; and (e) the risk assessment generator stored in memory and executable by the processor to further provide the risk assessment and the decision-support guidance to a display device that selectively couples with the risk assessment server.

According to some embodiments the processor further executes the instructions to determine whether a number of unique or overlapping individuals across the plurality of facets meet notification thresholds based on a jurisdiction.

According to various embodiments the risk assessment comprises a determination as to whether a number of unique or non-unique but overlapping individuals across the plurality of facets meet notification thresholds based on the applicable jurisdictions.

According to some embodiments each data incident comprises any of risk factors, the multi-region data incident data, and a plurality of jurisdictions.

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure, and explain various principles and advantages of those embodiments.

The methods and systems disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

FIG. 6 illustrates an exemplary GUI in the form of a data sensitivity level evaluation and selected federal and state specific risk assessments page;

FIG. 7 illustrates an exemplary GUI in the form of a federal risk assessment page;

FIG. 8 illustrates an exemplary GUI in the form of a state specific risk assessment page;

FIG. 9 illustrates an exemplary GUI in the form of a statute summary page;

FIG. 18 is a table of various party roles (properties), party types/relationships, and internal/external notifications.

FIG. 20 is a graphical user interface in the form of an external entity incident input screen where a party, contract, notification, and additional details are input into the risk assessment server.

FIG. 22 is a graphical user interface that displays a summary of an incident, as well as detailed information for one or more external entities impacted by a data incident.

FIG. 23 is a graphical user interface that provides detailed information regarding a data incident.

FIGS. 25-35 collectively illustrate various example features that can be implemented within the risk assessment server. The features are listed in tabular format.

FIG. 36 illustrates a Table that includes output of a multifaceted risk assessment for a multifaceted data incident.

FIG. 39 illustrates a Table that includes Profile data across configurations (intake and web form) for a multi-region data incident.

FIG. 40 is a Graphical User Interface (GUI) for an assessment of a multi-region data incident of the present disclosure.

FIG. 41 is a Graphical User Interface (GUI) of intake for a multi-region data incident of the present disclosure.

DETAILED DESCRIPTION

Figure 1:
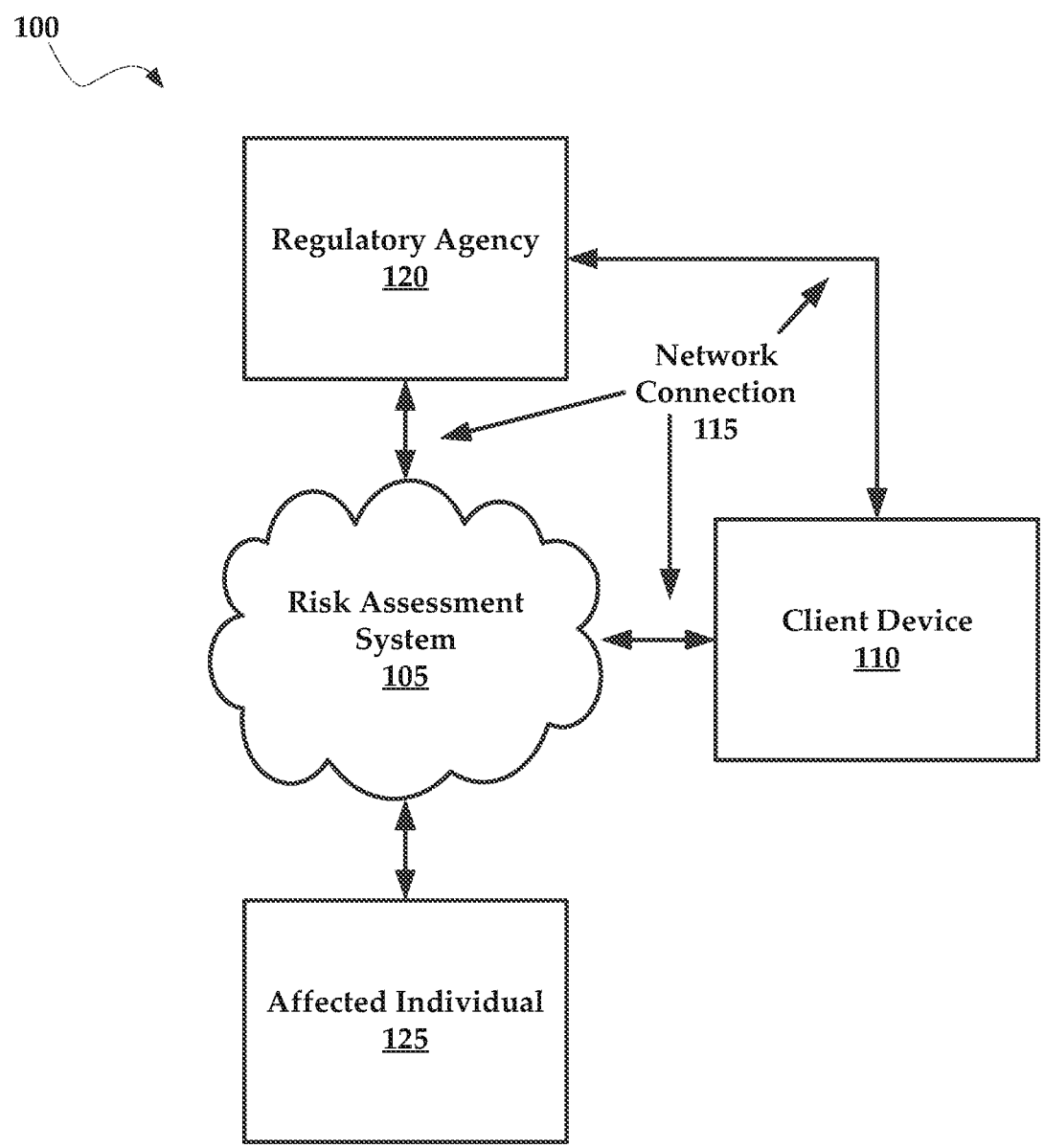
FIG. 1 illustrates an exemplary system for practicing aspects of the present technology.

In the following description, for purposes of explanation, numerous specific details are set forth in order to provide a thorough understanding of the disclosure. It will be apparent, however, to one skilled in the art, that the disclosure may be practiced without these specific details. In other instances, structures and devices are shown at block diagram form only in order to avoid obscuring the disclosure.

Generally speaking, the present technology may be directed to managing data incidents. It will be understood that the terms "data incident" may be understood to encompass privacy incidents, security incidents, privacy breaches, data breaches, data leaks, information breaches, data spills, or other similarly related events related to the intentional or unintentional release of protected information to an untrusted environment. This protected information may be referred to as personally identifiable information (hereinafter "PII/PHI") or protected health information (e.g., an entity that has been entrusted with the PHI such as a hospital, clinic, health plan, and so forth). Various embodiments of the present technology include systems and methods for managing multi-region data incidents that involve "Personal Data," which comprises any information about an individual that is considered protected under data privacy and protection laws, including but not limited to PII/PHI.

PII/PHI may encompass a wide variety of information types, but non-limiting examples of PII comprise an individual's full name, a date of birth, a birthplace, genetic information, biometric information (face, finger, handwriting, etc.), national identification number (e.g., social security), vehicle registration information, driver's license numbers, credit card numbers, digital identities, and Internet Protocol addresses. Various embodiments of the present technology include systems and methods for managing multi-region data incidents that involve "Personal Data," which comprises any information about an individual that is considered protected under data privacy and protection laws, including but not limited to PII/PHI.

Other types of information may, in some instances, be categorized as PII/PHI, such as an individual's first or last name (separately), age, residence information (city, state, county, etc.), gender, ethnicity, employment (salary, employer, job description, etc.), and criminal records—just to name a few. It is noteworthy to mention that the types of information that are regarded as PII are subject to change and therefore may include more or fewer types of information that those listed above. Additionally, what constitutes PII/PHI may be specifically defined by a local, state, federal, or international data privacy laws.

While entities that are subject to these privacy laws may be referred to in a variety of ways, for consistency and clarity an entity (either individual or corporate, or government agencies) that is entrusted with PII/PHI will hereinafter be referred to as an "entrusted entity."

It will be understood that the privacy laws contemplated herein may comprise details regarding not only how an entrusted entity determines if a data incident violates the law, but also when the provision of notification to one or more privacy agencies and/or the customers of the entrusted entity is warranted.

According to some embodiments, the present technology is directed to generating risk assessments for data incidents. These risk assessments provides specific information to the entrusted entity regarding the severity of the data incident relative to a state or federal rule. Additionally, the risk assessment provides information regarding the data sensitivity for the data incident. That is, the risk assessment may determine if the type of data that was exposed is highly sensitive information. As mentioned before, some PII/PHI may be considered more sensitive than others. For example, a social security number may be more sensitive than a gender description, although the relative sensitivity for different categories of PII/PHI are typically delineated in the privacy rules and may require delineation in the context of each data incident.

The present technology may determine the severity and/or data sensitivity for a data incident by collecting data incident data from an entrusted entity. This data incident data may be compared against one or more selected privacy rules to determine the severity and/or data sensitivity for the data incident. In some instances, the present technology may model the data incident data to the one or more privacy rules.

According to some embodiments, the privacy rules described herein may comprise the content of a state and/or federal statute. In other embodiments, the privacy rules may comprise abstracted or mathematically expressed rules that have been generated from the text of the state and/or federal statute. Applying a privacy rule to the data incident data may yield values for the severity and/or the data sensitivity of the data incident.

In some embodiments, the risk assessment may provide indication to the entrusted entity that an obligation has occurred. More specifically, if the severity of the data incident and/or the data sensitivity of the data incident when compared to the privacy rules indicates that the data incident has violated at least one of the privacy rules, the risk assessment may include an indication that an obligation has been created. An obligation may require the entrusted entity to notify subjected individuals that their PII/PHI has been potentially exposed. The obligation may also require that notification be provided to a regulating authority such as the department of Health and Human Services (HHS), Office for Civil Rights (OCR), Federal Trade Commission, a state agency, data protection authority (DPA), any agency that regulates data incident notification, credit reporting agencies, or any associations/standards bodies as designated by the applicable rules.

The present technology allows entrusted entities to model data incident data to privacy rules which include at least one state rule and at least one federal rule. In some instances, entrusted entities may model data incidents to the rules of several states to generate risk assessments of each of the states. This is particularly helpful when entrusted entities service customers in many states. Moreover, each of these states may have differing notification requirements, along with different metrics for determining when a data incident requires notification.

In some embodiments, the risk assessment may include a risk level that is associated with a color. More specifically, a hue of the color is associated with the severity of the data incident as determined by the comparison or modeling if the data incident data.

According to the present disclosure, the present technology may generate a notification schedule for an entrusted entity along with mechanisms that aid the entrusted entity in gathering pertinent information that is to be provided to the customer and/or one or more regulatory agencies.

These and other advantages of the present technology will be described in greater detail with reference to the collective FIGS. 1-15.

FIG. 1 illustrates an exemplary system 100 for practicing aspects of the present technology. The exemplary system 100 may include a risk assessment system 105 (hereinafter "system 105") that may be implemented in a cloud-based computing environment, or as a web server that is particularly purposed to manage data incidents.

In general, a cloud-based computing environment is a resource that typically combines the computational power of a large grouping of processors and/or that combines the storage capacity of a large grouping of computer memories or storage devices. For example, systems that provide a cloud resource may be utilized exclusively by their owners; or such systems may be accessible to outside users who deploy applications within the computing infrastructure to obtain the benefit of large computational or storage resources.

The cloud may be formed, for example, by a network of web servers, with each web server (or at least a plurality thereof) providing processor and/or storage resources. These servers may manage workloads provided by multiple users (e.g., cloud resource customers or other users). Typically, each user places workload demands upon the cloud that vary in real-time, sometimes dramatically. The nature and extent of these variations typically depend on the type of business associated with the user.

In other embodiments, the system 105 may include a distributed group of computing devices such as web servers that do not share computing resources or workload. Additionally, the system 105 may include a single computing device, such as a web server, that has been provisioned with one or more programs that are utilized to manage data incidents.

End users may access and interact with the system 105 via the client device 110 through a web-based interface, as will be discussed in greater detail infra. Alternatively, end users may access and interact with the system 105 via a downloadable program that executes on the client device 110. The system 105 may selectively and communicatively couple with a client device 110 via a network connection 115. The network connection 115 may include any one of a number of private and public communications mediums such as the Internet.

Additionally, the system 105 may collect and transmit pertinent information to regulatory agencies, such as regulatory agency 120, as will be discussed in greater detail infra. In some instances, notification may also be provided to affected individuals 125.

The system 105 may be generally described as a mechanism for managing data incidents. The system 105 may manage a data incident by collecting data incident data for the data incident and then modeling the data incident data to privacy rules. As mentioned previously, the privacy rules may include at least one state rule and at least one federal rule. The modeling of the data incident data may be utilized to generate a risk assessment for the data incident. The risk assessment may be utilized by an entrusted entity to determine how best to respond to the data incident. The system 105 is provided with a risk assessment application 200 that will be described in greater detail with reference to FIG. 2.

Figure 2:
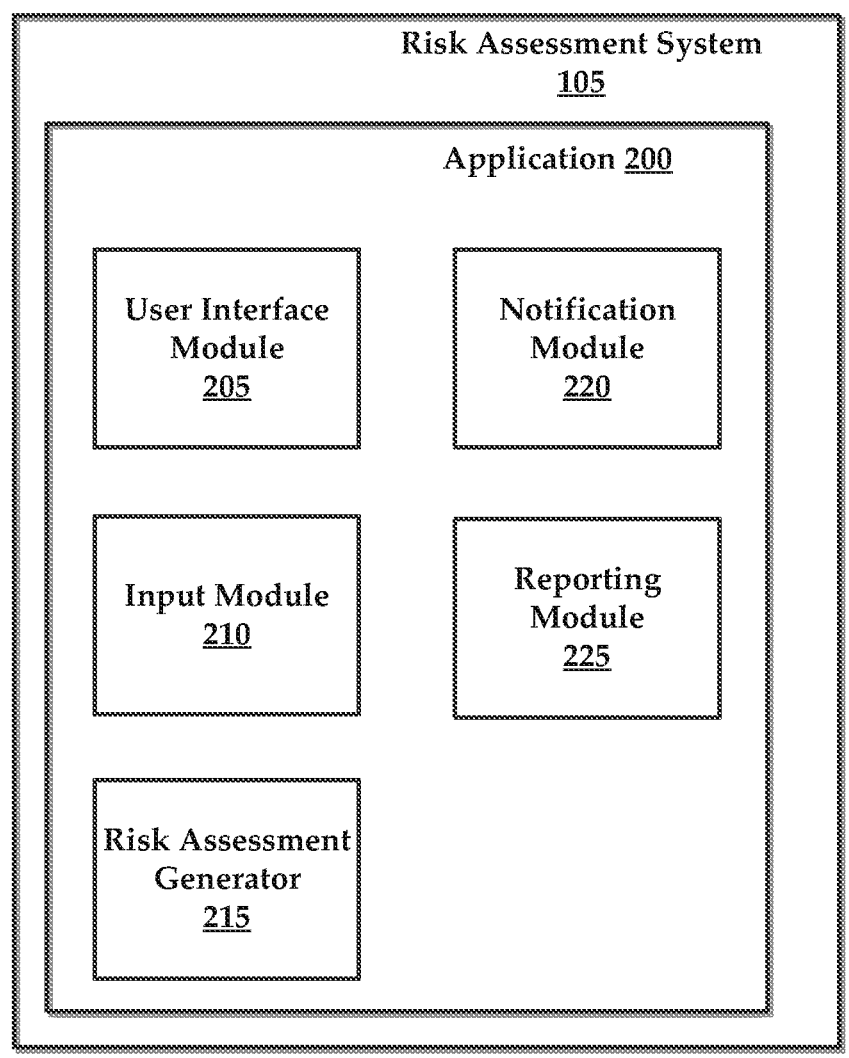
FIG. 2 illustrates an exemplary conversion application for managing data incidents.

FIG. 2 illustrates a risk assessment application, hereinafter referred to as application 200. In accordance with the present disclosure, the application 200 may generally include a user interface module 205, an input module 210, a risk assessment generator 215, a notification module 220, and a reporting module 225. It is noteworthy that the application 200 may include additional modules, engines, or components, and still fall within the scope of the present technology. Moreover, the functionalities of two or more modules, engines, generators, or other components may be combined into a single component.

As used herein, the terms "module," "generator," and "engine" may also refer to any of an application-specific integrated circuit ("ASIC"), an electronic circuit, a processor (shared, dedicated, or group) that executes one or more software or firmware programs, a combinational logic circuit, and/or other suitable components that provide the described functionality. In other embodiments, individual modules of the application 200 may include separately configured web servers. Also, the application 200 may be provisioned with a cloud.

Generally described, the application 200 allows entrusted entities to input data incident data, have one or more risk assessments generated, and receive the one or more risk assessments, along with notifications schedules, as required.

An entrusted entity may interact with the application 200 via a graphical user interface that is provisioned as a web-based interface. The web-based interface may be generated by the user interface module 205. It will be understood that the user interface module 205 may generate a plurality of different graphical user interfaces that allow individuals associated with the entrusted entity (e.g., privacy officer, compliance officer, security officer, attorney, employee, agent, etc.) to utilize interact with the application 200. Examples of graphical user interfaces that are generated by the user interface module 205 are provided in FIGS. 3-13, which will be described in greater detail infra.

Upon the occurrence of a data incident, the input module 210 may be executed to receive data incident data from the entrusted entity. It is noteworthy that the user interface module 205 may generate different types of graphical user interfaces that are tailored to obtain specific types of data incident data from the entrusted entity.

Initially, it may be desirous for the entrusted entity to establish a profile that may be utilized to determine if the entity that is using the application 200 is, in fact, an entrusted entity. It is noteworthy that to mention that the determination of what entities are entrusted entities depends upon the privacy rule. For example, an entity may be considered to be an entrusted entity under a particular federal statute, but may not be labeled an entrusted entity under one or more state statutes. Likewise, different states may have discrepant methods for determining who constitutes an entrusted entity.

Therefore, it may be advantageous to determine information about the entity such as what types of information they collect and where they conduct business. The input module 210 may be executed to solicit pertinent information from the entity that may be utilized to determine if the entity is an entrusted entity. Again, the entity may specify a plurality of states in which they conduct business, or the states of residence/domicile for customers with which they conduct business.

If it is determined that the entity is an entrusted entity, the input module may further solicit data incident data for one or more data incidents. Pertinent data incident data may include the type of data that was compromised, the date of compromise, the amount of data that was compromised, were there security measures in place (e.g., encryption, redaction, etc.), was the incident intentional or unintentional, was the incident malicious or non-malicious, how the data was compromised (e.g., theft of laptop, database security failure, lost storage media, hacked application, hacked computing device (e.g., web server, email server, content repository, etc.), and other types of information that assist in determining a risk level for the data incident as well as any notification obligations.

In some instances, rather than soliciting generalized data incident data from the entrusted entity, the input module 210 may select questions that solicit data that is particularly relevant to the privacy rules to which the entrusted entity is subject. For example, if a privacy rule specifies that a threshold amount of records must be exposed in order to create an obligation, the end user may be asked if their amount of exposed records meets or exceeds that threshold amount. This type of tailored questioning narrows the analysis that is performed of the data incident data and improves the efficiency of the risk assessment process.

Once the data privacy data has been received, the input module 210 may generate a summary of the data privacy data (or at least a portion of the data) that is provided to the entrusted entity via a graphical user interface generated by the user interface module 205.

The input module 210 may be configured to solicit confirmation from the entrusted entity that the data privacy data in the summary is correct. If the data is incorrect, the entrusted entity may go back and correct the errant data.

As mentioned briefly above, the input module 210 may solicit and receive one or more selections of one or more states from the entrusted entity. Using the selections, the input module 210 may select one or more state statutes based upon the one or more selections. Also, the input module 210 may generate at least one state rule for each selected state statute. Additionally, one or more federal rules may be selected and generated as well.

The input module 210 may generate a state or federal privacy rule by evaluating the state/federal statute and creating a plurality of qualifications from the statutes. Qualifications for a statute may include, for example, thresholds or formulas that are used to determine if the data incident data of a data incident violates the statute. Stated otherwise, these qualifications may be used as a mathematical model of a statute. Data incident data may be evaluated in light of the model. The resultant modeling may be used to generate a risk assessment for the data incident.

The risk assessment generator 215 may be executed to generate one or more risk assessments for the data incident. The risk assessment generator 215 may model the data incident data to the selected or determined privacy rules to determine if an obligation has been triggered under a privacy rule.

Again, risk assessments may be generated by modeling the data incident data to at least one state rule and at least one federal rule. The risk assessment may combine risk levels for each rule into a single risk assessment, or individual risk assessments may be generated for each rule.

Modeling of the data incident data to a privacy rule (either state or federal) by the risk assessment generator 215 may result in the generation of a severity value and a data sensitivity value for the data incident. The severity value may represent the extent to which PII/PHI has been compromised, while the data sensitivity value may represent the relative sensitivity of the PII/PHI that was compromised. These two factors may independently or dependently serve as the basis for determining if a notification obligation exists. For example, if the severity value meets or exceeds a threshold amount, a notification obligation may exist. If the data sensitivity value meets or exceeds a threshold amount, a notification obligation may exist. In some instance, a notification obligation may only exist if the sensitivity value and the data sensitivity value both exceed threshold amounts. Again, the threshold amounts are specified by the particular privacy rule that is being applied to the data incident data.

The risk assessment generator 215 may also determine and apply exceptions that exist in a state or federal statute during the generation of a risk assessment. These exceptions may be noted and included in the risk assessment.

Figure 7:
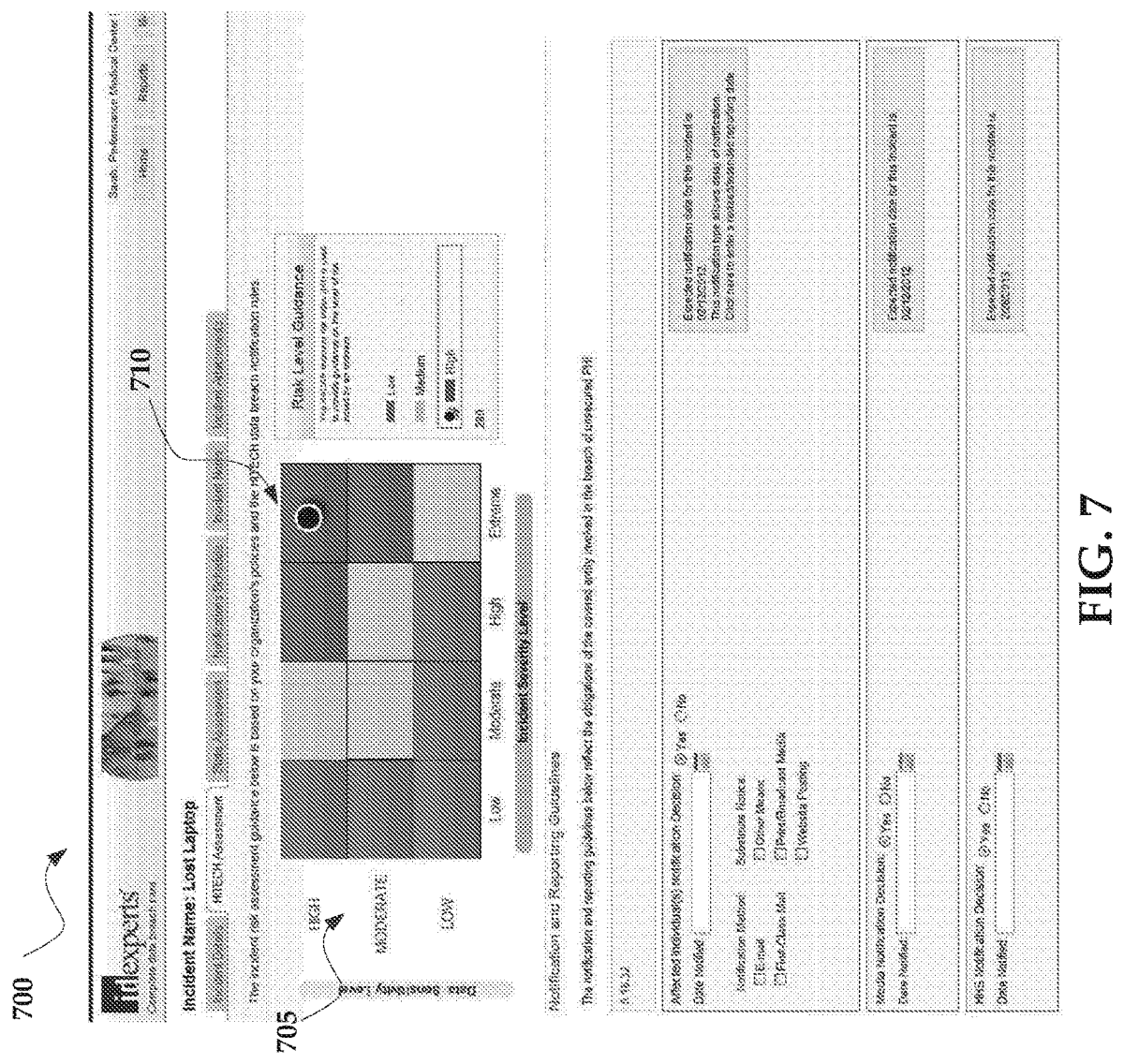

The risk assessment generator 215 may create a visual indicator such as a risk level or heat map that assists the entrusted entity in determining if a data incident is relatively severe or is relatively benign. This visual indicator may be included in the risk assessment. For example, a risk assessment may include a risk level that includes a visual indicator such as a colored object. In some embodiments, a hue of the object is associated with the severity of the data incident where red may indicate a severe risk and green may indicate a benign risk, with orange or yellow hues falling somewhere therebetween. Examples of heat maps and risk levels indicators are illustrated in FIG. 7.

Included in the risk assessment, in some instances, is a summary of sections of the state or federal privacy statute. For example, with regard to a state specific assessment, the risk assessment generator 215 may generate an outline of key information about the state statute that was utilized to generate the state specific risk assessment. This outline may be displayed to the entrusted entity via a user interface.

If the risk assessment generator 215 determines that the data incident violates one or more statutes (e.g., high severity value, PII/PHI is very sensitive, etc.), the notification module 220 may be executed to generate a notification schedule. Again, various embodiments of the present technology include systems and methods for managing multi-region data incidents that involve "Personal Data," which comprises any information about an individual that is considered protected under data privacy and protection laws, including but not limited to PII/PHI. The notification schedule may be generated based upon a data associated with the data incident. That is, the statute may specify when notification is to occur, relative to the date that PII was exposed.

Additionally, the notification schedule informs the entrusted entity as to what types of information are to be provided, along with the regulatory bodies to which the information should be provided. Again, the notification schedule may be generated from the statute itself. For example, a statute may specify that the data incident data (or a portion of the data incident data) collected by the input module 210 should be provided to a particular state agency within a predetermined period of time. Again, if a plurality of states have been designated or selected, the notification schedule may include notification dates for each state agency.

To assist the entrusted entity in meeting their notification obligations, the reporting module 225 may be executed to gather pertinent documents or other information from the entrusted entity and transmit these documents to the required reporting authorities. The reporting module 225 may prompt the entrusted entity to attach documents via a user interface. Once attached, these documents/data may be stored in a secured repository for submission to regulatory agency. In other instances, the entrusted entity may transmit required information directly to the regulatory agency.

Additionally, the reporting module 225 may provide required notifications to affected individuals, such as the individuals associated with the PII/PHI that was compromised.

FIGS. 3-13 illustrate various exemplary graphical user interfaces (GUI) that are generated by the user interface module 205. Each of the exemplary user interfaces will be described below.

Figure 3:
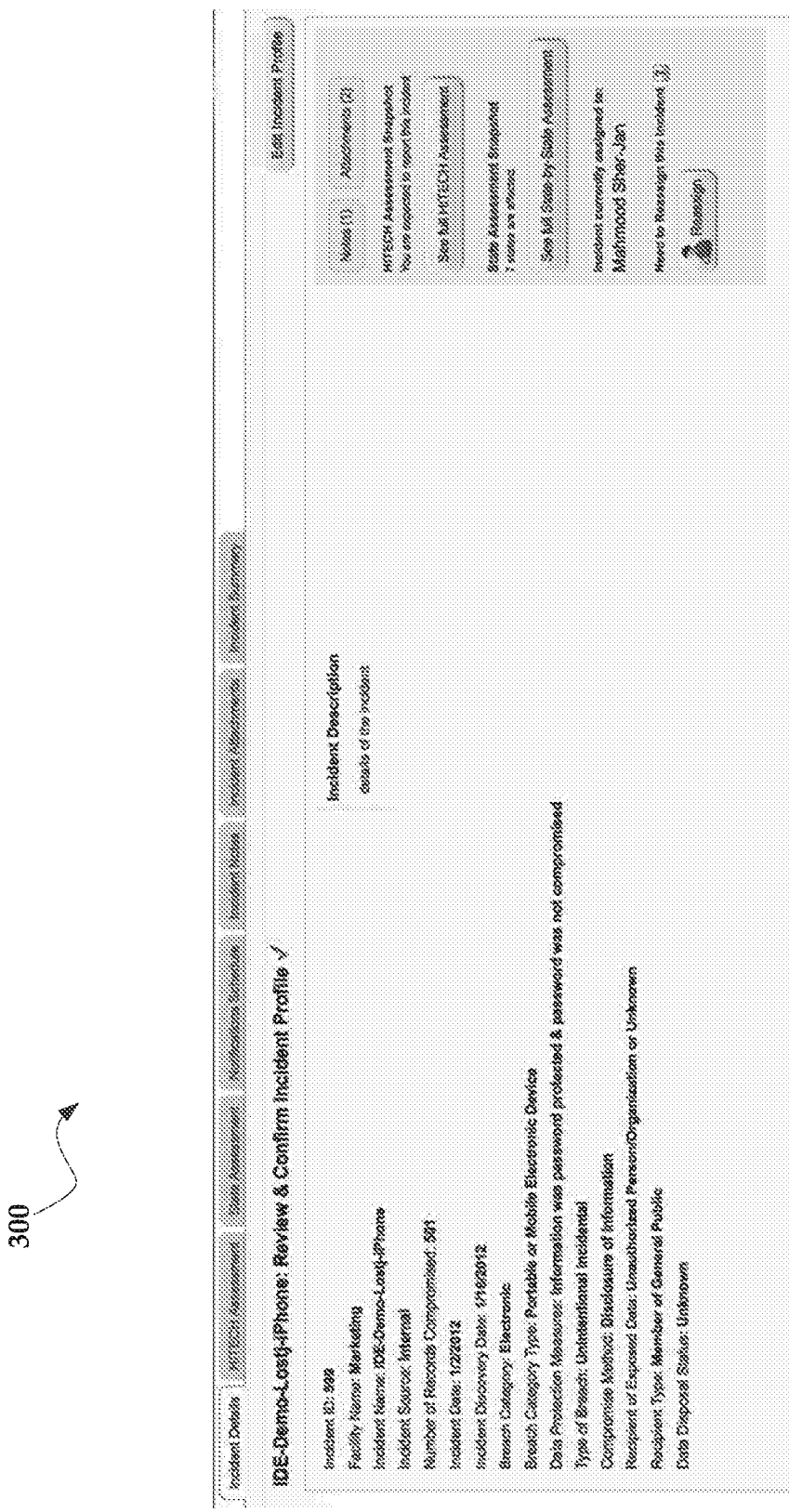
FIG. 3 illustrates an exemplary GUI in the form of a data incident details page.

FIG. 3 illustrates an exemplary GUI in the form of a data incident summary page. The summary page 300 includes a plurality of received answers to questions that were provided to the entrusted entity. Responses that were received indicate that the data incident involved the loss of a cellular telephone, an incident date of Jan. 2, 2012, an incident discover date of Jan. 16, 2012, and other pertinent data incident data.

Figure 4:
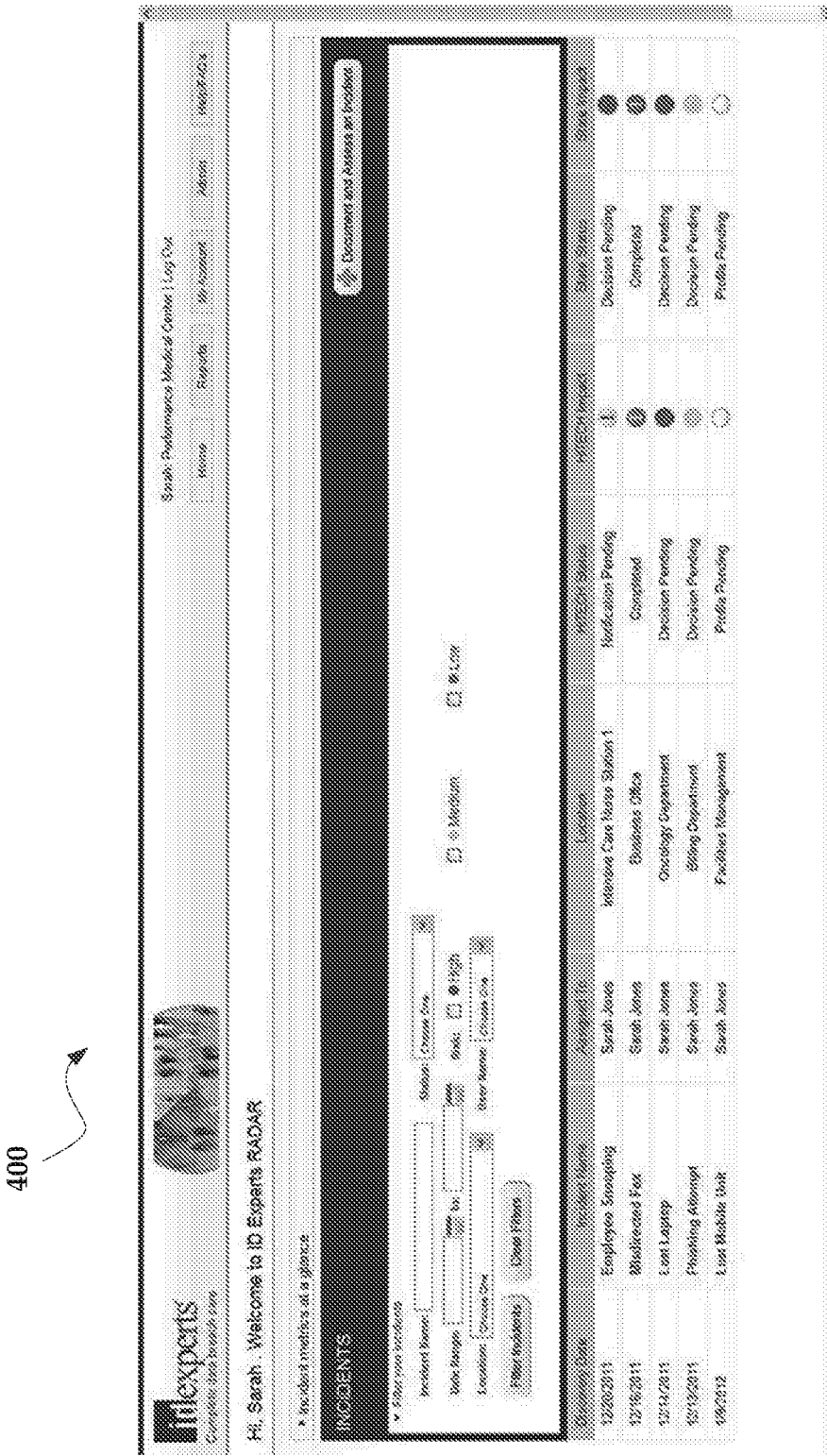
FIG. 4 illustrates an exemplary GUI in the form of a data incident dashboard.

FIG. 4 illustrates an exemplary GUI in the form of a data incident dashboard page 400. The page 400 includes listing of pending and completed risk assessments for a plurality of data incidents. Each entry may include a risk indicator having a particular color to help the entrusted entity in quickly determining data incidents that are high risk. A risk indicator may be associated with a particular privacy rule. For example, a risk indicator for an Employee Snooping data incident indicates that a moderately high risk is associated with the data incident relative to HITECH rules (e.g., rules associated with the compromise of PHI). This moderately high risk is indicated by a yellow dot placed within a row of a "HITECH Status" column. Additionally, a severe risk is associated with a state privacy rule. This severe risk is indicated by a red dot placed within a row of a "State Impact" column.

Figure 5:
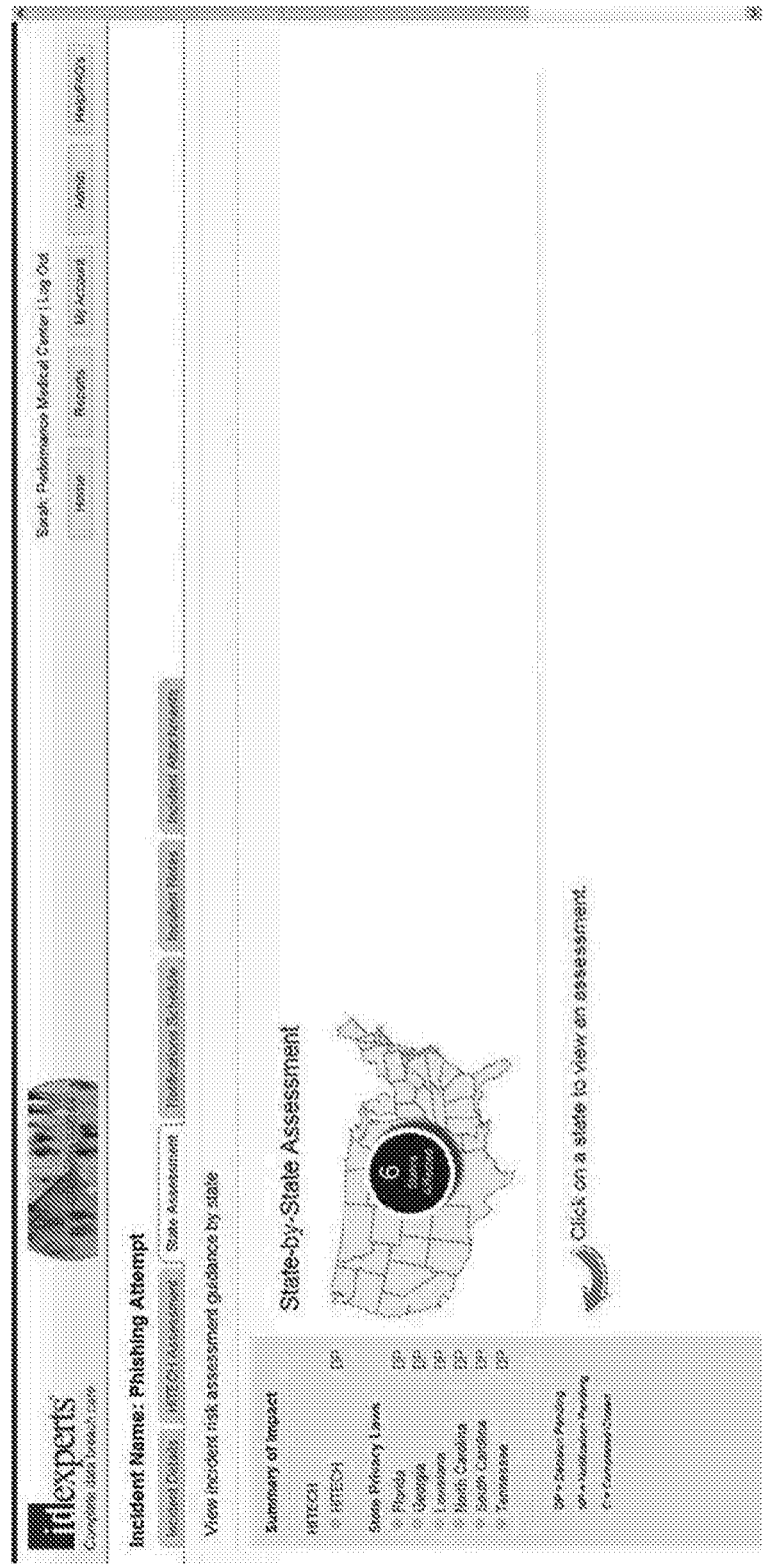
FIG. 5 illustrates an exemplary GUI in the form of a state specific risk assessment selection and notification page.

FIG. 5 illustrates an exemplary GUI in the form of a state specific selection and notification page 500. The notification page is shown as comprising an image that informs the trusted entity that six states have been affected by the data incident. To view a risk assessment for each state, the trusted entity may click on any of the states listed in the leftmost frame.

Figure 6:
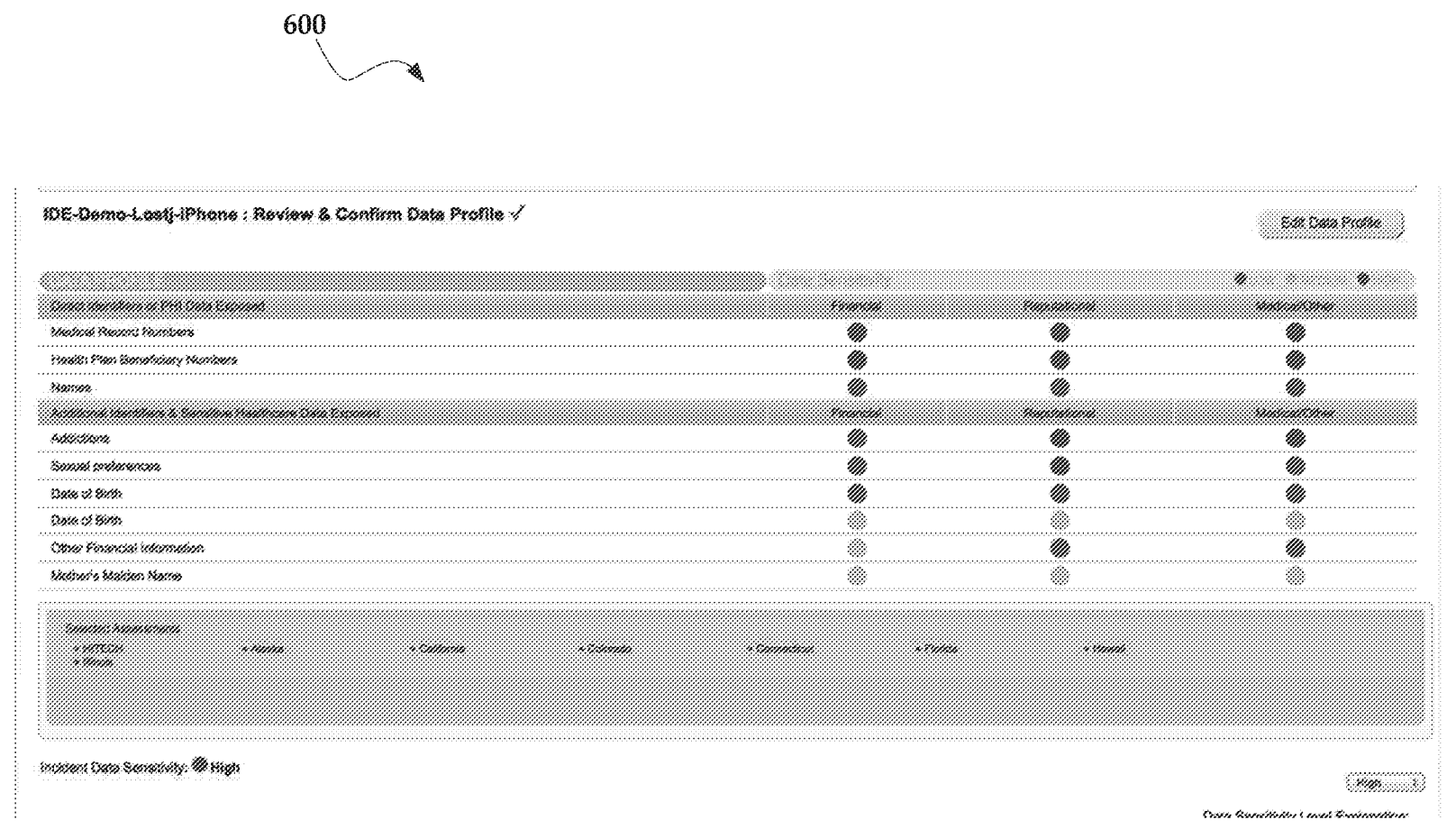

FIG. 6 illustrates an exemplary GUI in the form of a data sensitivity level evaluation page 600. The page includes a plurality of data sensitivity indicators the sensitivity for different types of PII/PHI that were compromised by the data incident. For example, medical record numbers are shown in red as being highly sensitive. Moreover, medical record numbers may pose financial, reputational, and medical harm, which are just some of the dimensions of potential harm caused by compromise of PII/PHI. In contrast, the data incident also compromised individual's date of birth. As determined by entrusted entity, that type of PII/PHI is not considered highly sensitive and thus, has been depicted in green.

FIG. 7 illustrates an exemplary GUI in the form of a risk assessment page 700. The risk assessment page 700 includes a heat map 710 and corresponding risk level indicator 705, which is placed within the heat map 710. The heat map 710 includes a grid where vertical placement indicates data sensitivity level and horizontal placement indicates severity level. As is shown, as the sensitivity and severity levels increase, so do the odds that the data incident may trigger an obligation to notify affected parties. In this instance, the risk level is high because the sensitivity level is high and the severity level is extreme.

Positioned below the heat map 710 is a notification schedule that includes not only the obligations for the entrusted entity, but also the expected notification dates. Again, this schedule may be based upon requirements included in the violated statute.

Figure 8:
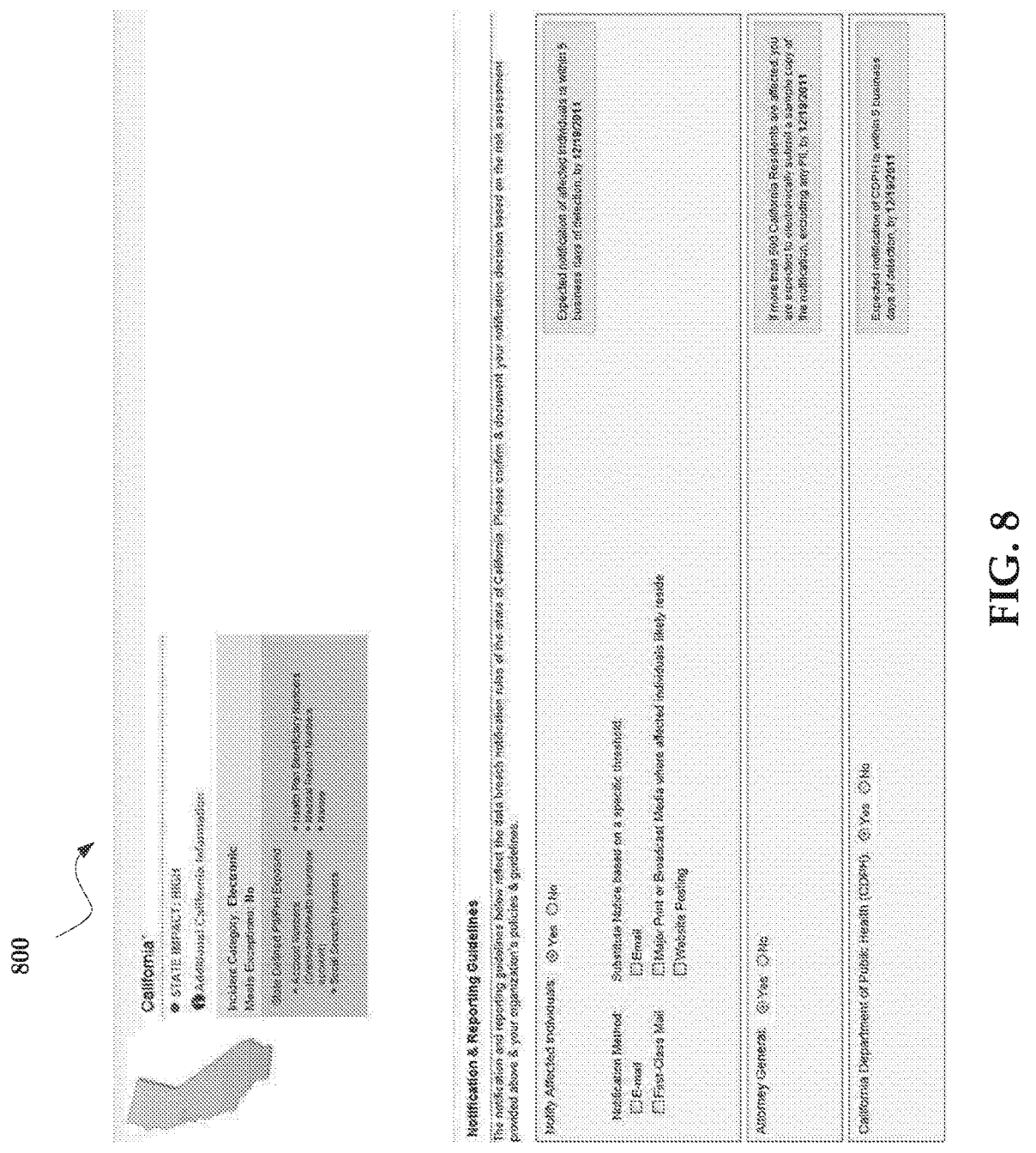

FIG. 8 illustrates an exemplary GUI in the form of a state specific risk assessment page 800. The page 800 includes a risk assessment for the State of California. The state impact is shown as high and a summary of the types of PII/PHI that were exposed are summarized below the state impact indicator. Similarly to the risk assessment page 700 of FIG. 7, a notification schedule is included on the state specific risk assessment page 800. It is noteworthy that a state specific risk assessment page may be generated for each affected state (such as the affected states listed on the state specific selection and notification page 500 of FIG. 5.

FIG. 9 illustrates an exemplary GUI in the form of a statute summary page 900. The statute summary page 900 includes a copy (or a portion) of the privacy statutes (California Civil Code 1798.29 & 1798.82; California Health and Safety Code 1280.15) that were utilized to generate the state specific risk assessment that was provided on in FIG. 8. Note that the summary also includes whether the state statutes include harm test and exceptions which are flagged by the risk assessment generator 215 according to the specific privacy statutes.

Figure 10:
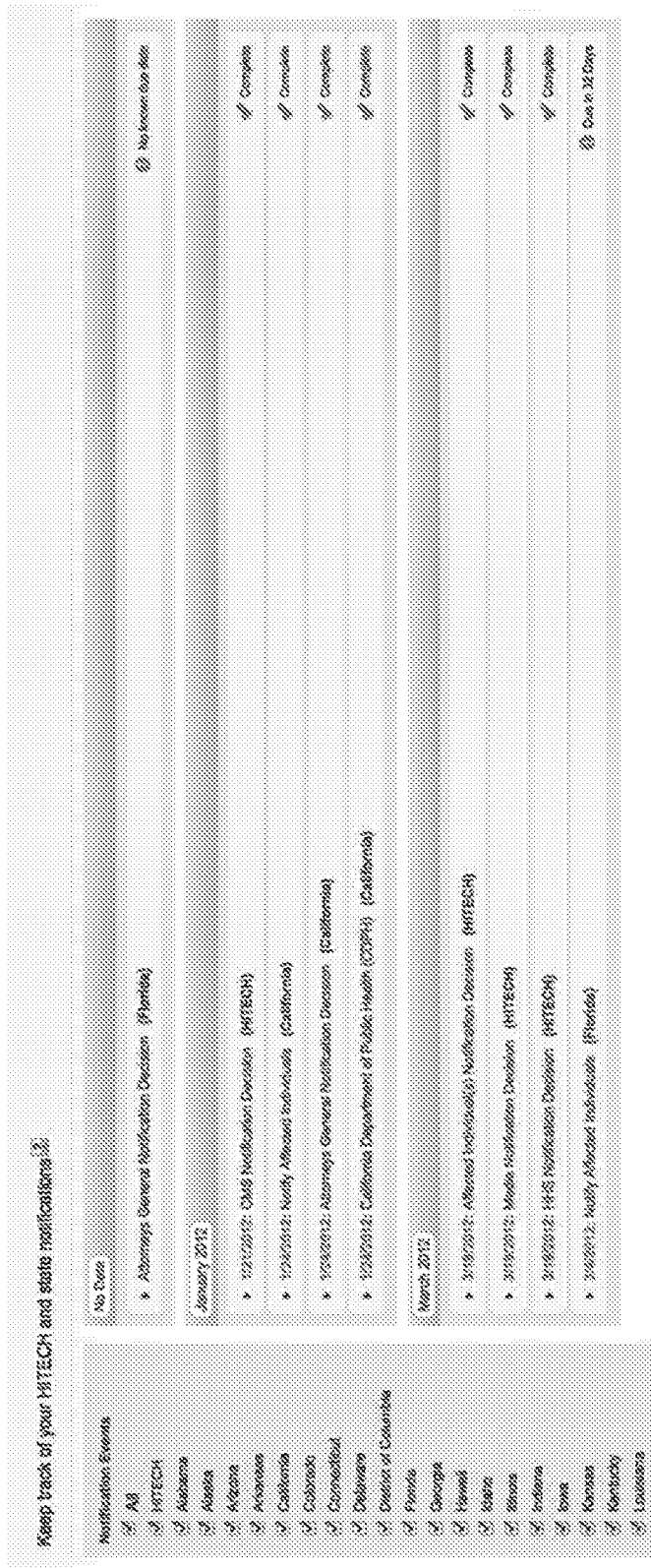
FIG. 10 illustrates an exemplary GUI in the form of an aggregated notification schedules page.

FIG. 10 illustrates an exemplary GUI in the form of an aggregated notification page 1000. The page 1000 includes a notification schedule for each affected privacy statues (e.g., federal and state(s)) relative to one or more data incidents. A list of notification events is provided and the end user may utilize the check boxes to select which states (or federal) risk assessment notification schedules are displayed.

Figure 11:
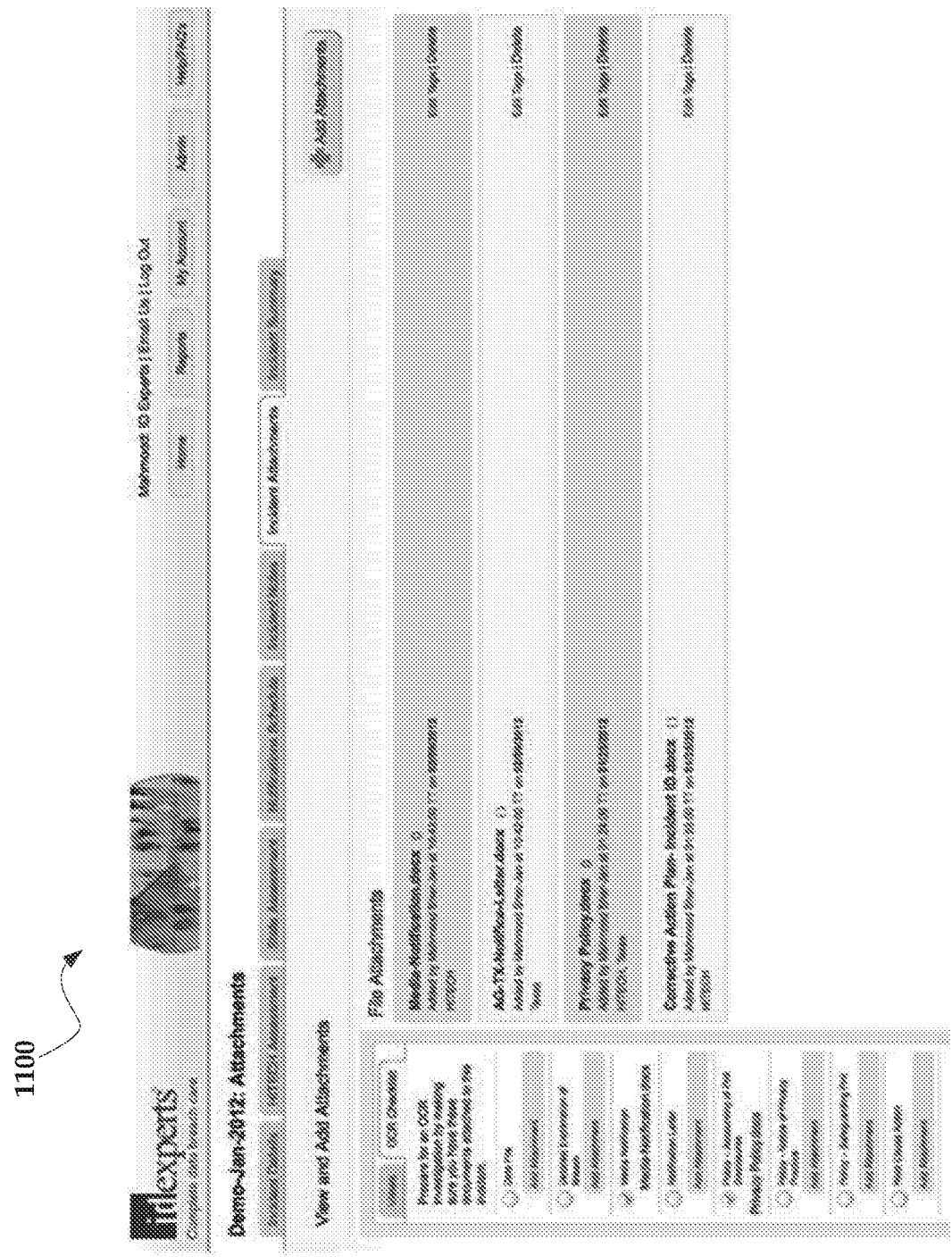
FIGS. 11-13 illustrate exemplary GUIS that are utilized to collect, store, and transmit pertinent documents or data.
Figure 12:
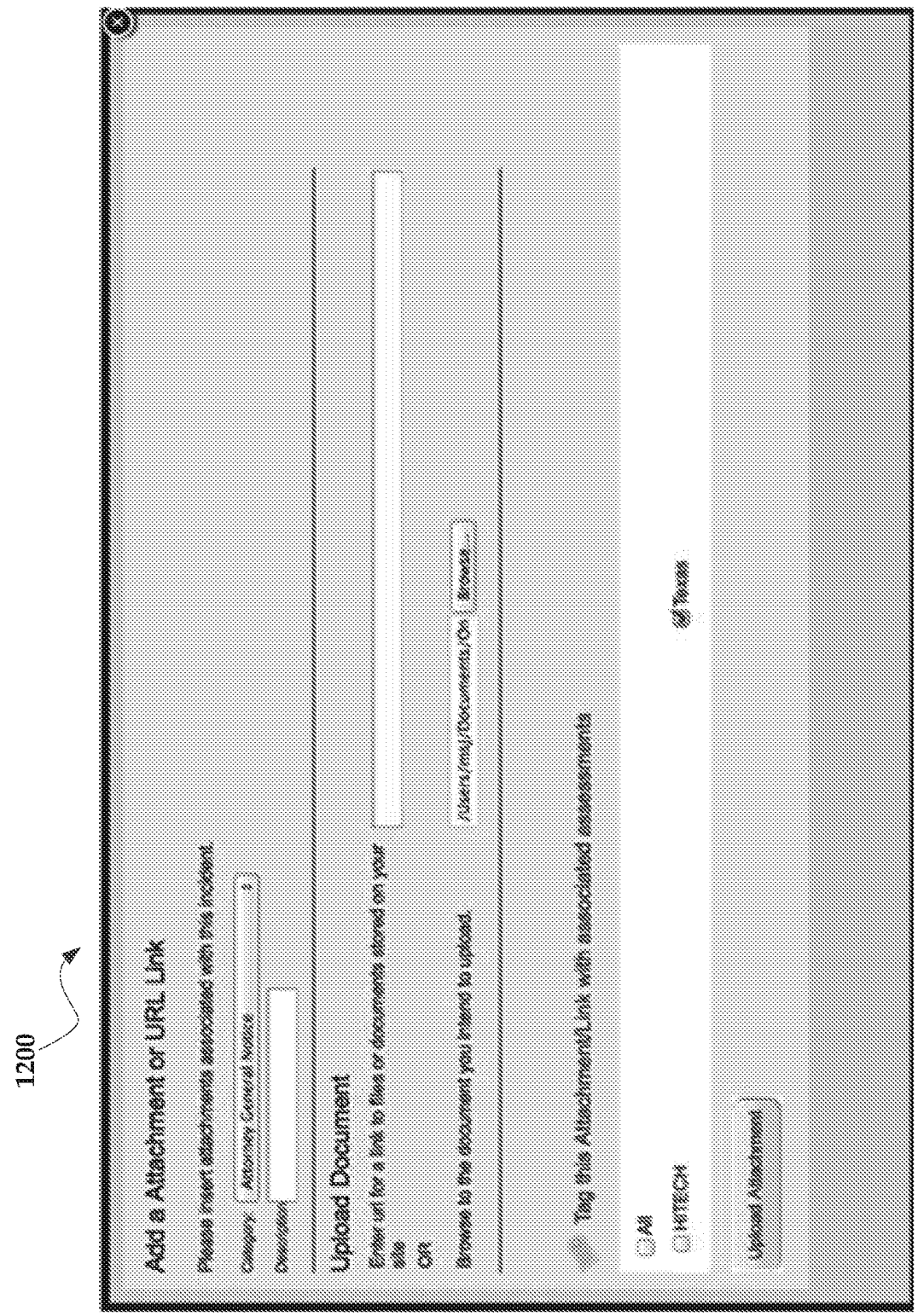
Figure 13:
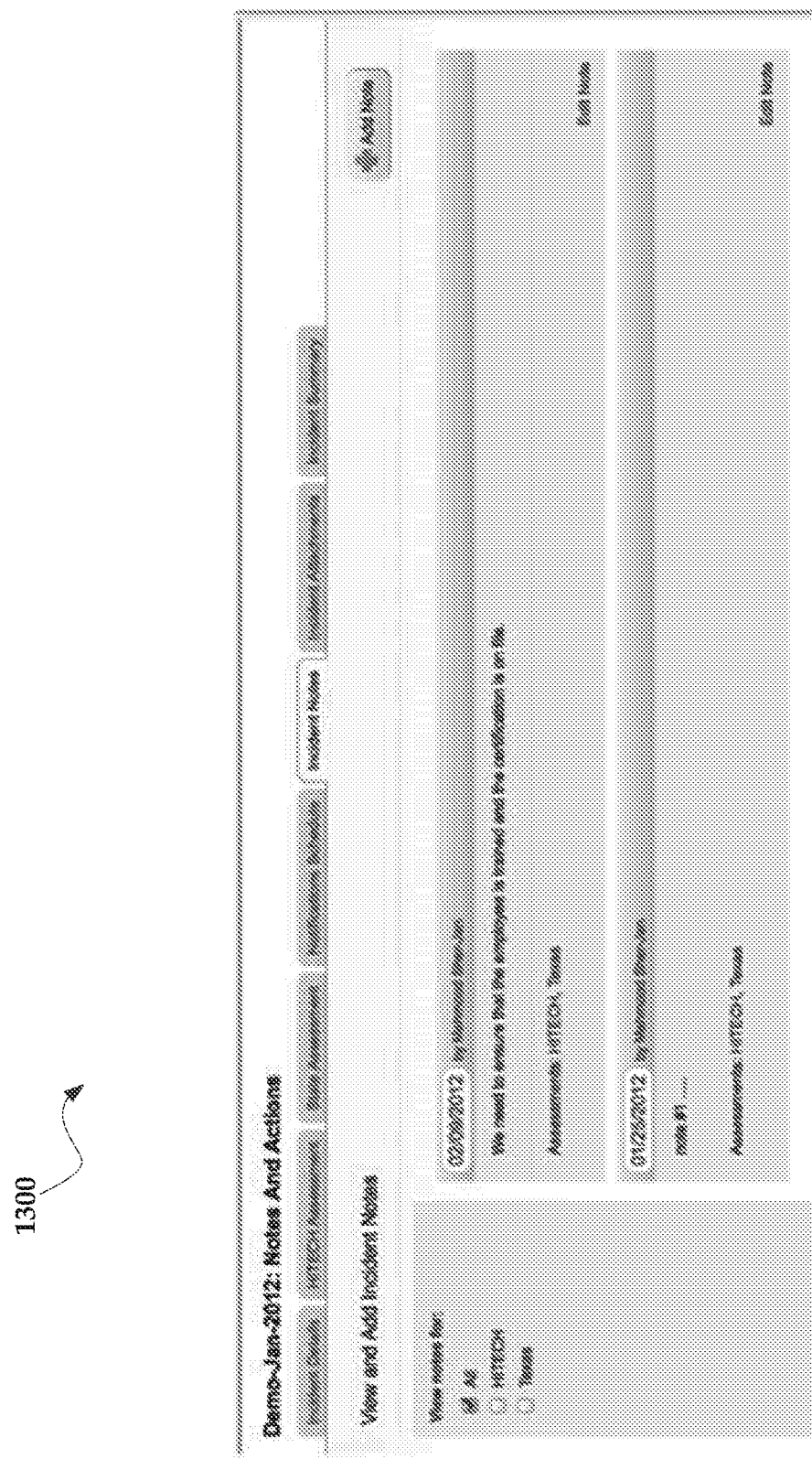

FIGS. 11-13 illustrate exemplary GUIS that are utilized to collect, store, and transmit pertinent documents or data. FIG. 11 illustrates an attachments page 1100 that shows a plurality of documents that have been uploaded to the system such as media notification, attorney general notification, privacy policy, and corrective action plan. Positioned adjacent to the list of documents is a checklist that includes all the pertinent documentation that is to be provided to regulatory authorities, the media, and/or affected individuals. As the required data are uploaded, each required data category is noted with a green check mark. Missing elements can be easily determined and uploaded.

It is noteworthy to mention that the on-time reporting of required incident data may be paramount in determining compliance and good faith on the part of an entrusted entity. Consequently, failure to meet required notification deadlines may result in fines and other regulatory punishment.

FIG. 12 illustrates an upload page 1200 that may be utilized by an entrusted entity to upload and categorize required compliance information (e.g., documents shown in FIG. 11). Files may be tagged with metadata linking them to the related federal and states risk assessments before they are stored in a content repository or transmitted to an appropriate party.

FIG. 13 illustrates an exemplary time stamped notation and actions page 1300 that displays notes entered into the system by a particular end user. Actions may include a note that a particular employee is to be retrained and certified. Any type of related action such as a remedial action, uploading of a file, or other notification and/or compliance related action may be noted and associated with a particular risk assessment.

Figure 14:
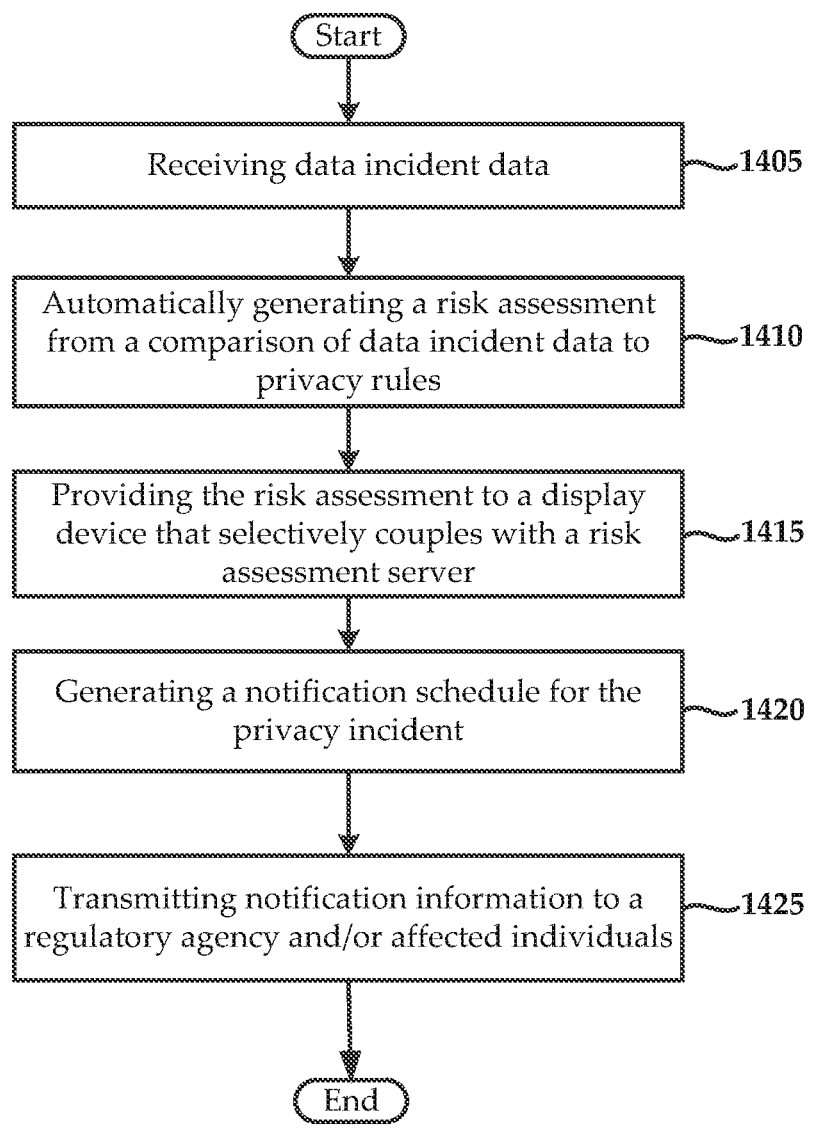
FIG. 14 is a flowchart of an exemplary method for managing a data incident.

FIG. 14 illustrates a flowchart of an exemplary method for managing a data incident. The method may include a step 1405 of receiving data incident data. The data incident data may include information that pertains or corresponds to the data incident. Also, the method may include a step 1410 of automatically generating a risk assessment from a comparison of data incident data to privacy rules. The privacy rules may comprise at least one federal rule and at least one state rule, where each of the rules defining requirements associated with data incident notification laws. Additionally, the comparison may include modeling the data incident data against privacy rules. Also, the method may include a step 1415 of providing the risk assessment to a display device that selectively couples with a risk assessment server. It is noteworthy to mention that the risk assessment may include a visual representation of the risk associated with a data incident relative to the privacy rules.

Additionally, for data incidents that violate a privacy rule (either state or federal) the method may include a step 1420 of generating a notification schedule for the data incident, along with an optional step 1425 of transmitting notification information to a regulatory agency and/or affected individuals (e.g. those who's PII/PHI has been compromised).

Figure 15:
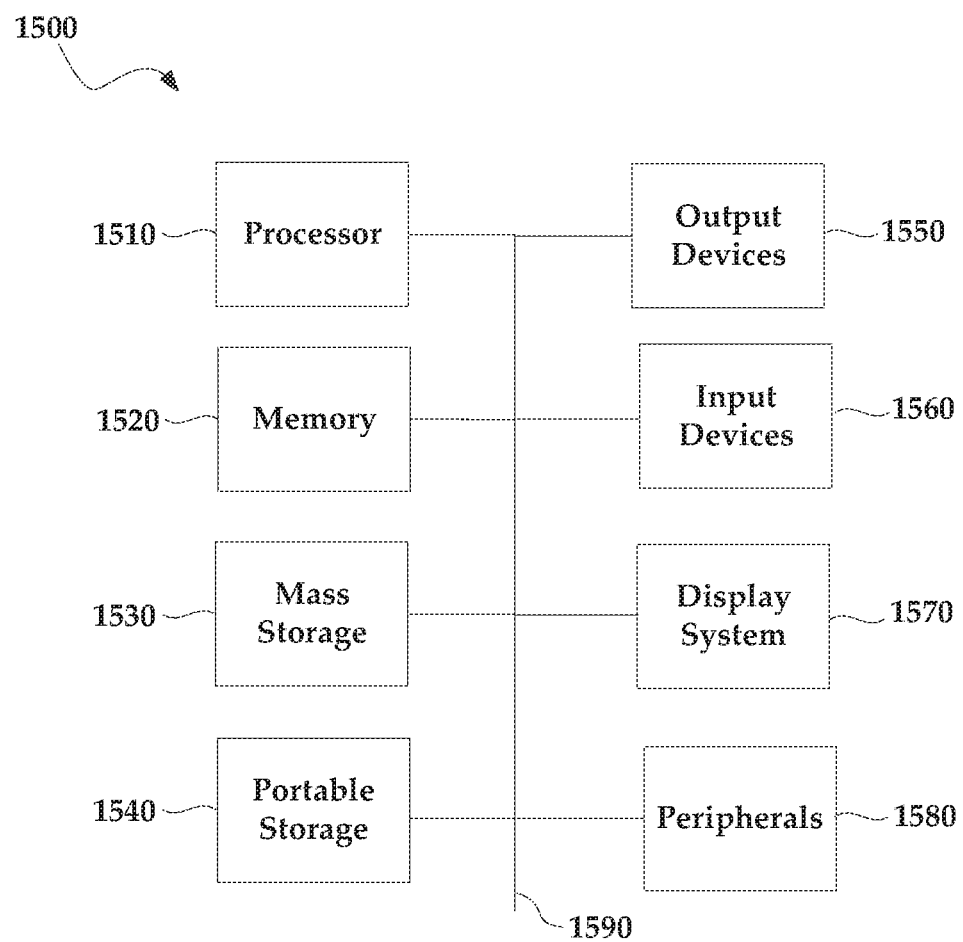
FIG. 15 illustrates an exemplary computing device that may be used to implement embodiments according to the present technology.

FIG. 15 illustrates an exemplary computing device 1500 that may be used to implement an embodiment of the present technology. The computing device 1500 of FIG. 15 (or portions thereof) may be implemented in the context of system 105 (FIG. 1). The computing device 1500 of FIG. 15 includes one or more processors 1510 and main memory 1520. Main memory 1520 stores, in part, instructions and data for execution by processor 1510. Main memory 1520 may store the executable code when in operation. The computing device 1500 of FIG. 15 further includes a mass storage device 1530, portable storage medium drive(s) 1540, output devices 1550, user input devices 1560, a graphics display 1570, and peripheral devices 1580.

The components shown in FIG. 15 are depicted as being connected via a single bus 1590. The components may be connected through one or more data transport means. Processor unit 1510 and main memory 1520 may be connected via a local microprocessor bus, and the mass storage device 1530, peripheral device(s) 1580, portable storage device 1540, and display system 1570 may be connected via one or more input/output (I/O) buses.

Mass storage device 1530, which may be implemented with a magnetic disk drive or an optical disk drive, is a non-volatile storage device for storing data and instructions for use by processor unit 1510. Mass storage device 1530 may store the system software for implementing embodiments of the present invention for purposes of loading that software into main memory 1520.

Portable storage device 1540 operates in conjunction with a portable non-volatile storage medium, such as a floppy disk, compact disk, digital video disc, or USB storage device, to input and output data and code to and from the computing device 1500 of FIG. 15. The system software for implementing embodiments of the present invention may be stored on such a portable medium and input to the computer device 1500 via the portable storage device 1540.

Input devices 1560 provide a portion of a user interface. Input devices 1560 may include an alphanumeric keypad, such as a keyboard, for inputting alpha-numeric and other information, or a pointing device, such as a mouse, a trackball, stylus, or cursor direction keys. Additionally, the computing device 1500 as shown in FIG. 15 includes output devices 1550. Suitable output devices include speakers, printers, network interfaces, and monitors.

Display system 1570 may include a liquid crystal display (LCD) or other suitable display device. Display system 1570 receives textual and graphical information, and processes the information for output to the display device.

Peripherals 1580 may include any type of computer support device to add additional functionality to the computer system. Peripheral device(s) 1580 may include a modem or a router.

The components provided in the computing device 1500 of FIG. 15 are those typically found in computer systems that may be suitable for use with embodiments of the present invention and are intended to represent a broad category of such computer components that are well known in the art. Thus, the computing device 1500 of FIG. 15 may be a personal computer, hand held computing device, telephone, mobile computing device, workstation, server, minicomputer, mainframe computer, or any other computing device. The computer may also include different bus configurations, networked platforms, multi-processor platforms, etc. Various operating systems may be used including Unix, Linux, Windows, Macintosh OS, Palm OS, Android, iPhone OS and other suitable operating systems. The computing device 1500 may also utilize web browser applications that display the web-based graphical user interfaces described herein. Exemplary web browser applications may include, but are not limited to, Internet Explorer, Firefox, Safari, Chrome, and other web browser applications that would be known to one of ordinary skill in the art with the present disclosure before them. Moreover, when the computing device 1500 is a mobile computing device, the computing device 1500 may likewise include mobile web browser applications.

It is noteworthy that any hardware platform suitable for performing the processing described herein is suitable for use with the technology. Computer-readable storage media refer to any medium or media that participate in providing instructions to a central processing unit (CPU), a processor, a microcontroller, or the like. Such media may take forms including, but not limited to, non-volatile and volatile media such as optical or magnetic disks and dynamic memory, respectively. Common forms of computer-readable storage media include a floppy disk, a flexible disk, a hard disk, magnetic tape, any other magnetic storage medium, a CD-ROM disk, digital video disk (DVD), any other optical storage medium, RAM, PROM, EPROM, a FLASHEPROM, any other memory chip or cartridge.

The embodiments described above consider the effect(s) of state and/or federal laws on a data incident, and specifically what types of obligations arise in view of these laws. The embodiments also consider the generating a notification schedule in light of the obligations imposed upon a breaching party.

The present technology can also be extended to consider not only local, state, federal, international laws, as well as combinations thereof, but also the impact of contractual obligations on a breaching party.

In some embodiments, the present technology can evaluate and apply three separate and types of obligations. The first type of obligations arise from the application of state law to a data incident. The application of the first type of obligations results in the imposition of a first set of obligations for a breaching party. The second type of obligations arise from the application of federal law to a data incident. The application of the second type of obligations results in the imposition of a second set of obligations for a breaching party.

The third type of obligations arise from the application of contractual obligations to a data incident. The application of the third type of obligations results in the imposition of a third set of obligations to a breaching party.

According to some embodiments, each of the first set, second set, and third set of obligations are different from one another. That is, each set of obligations will impose a unique obligation or set of obligations on the breaching party, which are different from the other sets of obligations. For example, a third set of obligations imposed by a contractual obligation comprises a requirement of a rapid email notification to all business customers within 24 hours of a data incident. While state and federal laws will have their own obligations, the state and federal laws will not have this obligation. Again, various embodiments of the present technology include systems and methods for managing multi-region data incidents that involve "Personal Data," which comprises any information about an individual that is considered protected under data privacy and protection laws, including but not limited to PII/PHI. The data privacy and protection laws are not limited to US state and Federal laws and further comprise international and foreign laws and agreements.

While a breaching party is generally defined as a party that has obligations imposed on it due to a data incident, in the context of a contractual obligation, a breaching party is one of at least two or more parties to a contractual obligation. This breaching party is the subject of a data incident. For example, a contract exists between a data owner and a data custodian, who are both parties to a contractual obligation. The contractual obligation specify certain obligations relating that are in addition to, or in excess of, the state or federal rules that dictate obligations in light of a data incident/breach.

In general, the present technology can be used to create response plans involving data incidents where parties to the data incident have hybrid roles. For example, the parties could include a covered entity and a business associated of the covered entity. The present technology provides workflow management that allows an entity to manage its state and federal regulatory obligations as well as its contractual obligations stemming from a data incident involving data that is owned by the entity, as well as data that is being processed or maintained by a second entity on behalf of the entity's clients.

Whereas state and federal obligations are imposed on any party that is involved in a data incident via statute or law, a contractual obligation relating to data privacy involves obligations that are imposed by contract onto one or more of the parties to the contract.

A data owner, a data maintainer, a data steward, and a data custodian are to be understood in terms of their relationship or role relative to a set of data that is the subject of a data incident. A data owner is a party that has complete legal rights over a set of data. The data owner also has rights in use, acquisition, distribution, destruction of this data—just to name a few. A data custodian controls authorization for access data, interpreting data security policies, data versioning control, and so forth. A data steward is responsible for data elements, controlling both data content and metadata, as well as usage consistency, data conflict resolution, and so forth. The data custodian and data steward work together to preserve data security of the set of data. The roles of a data custodian and a data steward will be construed in accordance with data governance rules applied between the parties to the contractual obligation.

It will be understood that multiple parties involved in a data incident can have obligations imposed upon them. Thus, in some instances only one party in a data incident is obligated with notification requirements. In other embodiments, multiple parties can be imposed with obligations due to a data incident.

In the context of HIPAA, in one embodiment a first party is a covered entity and a second party is a business associate of the covered entity. If a data incident occurs, regardless of the fault of any given party, both the covered entity and the business associate are subject to notification obligations. Due to the respective roles, the obligations for each party can be different. The state and federal laws can have obligations that are imposed on each party and these obligations can be different from one another.

Also, the covered entity and the business associate can have an executed contractual agreement that defines contractual obligations for the parties. For example, a covered entity can employ a business associate to carry out its administrative functions related to the provision of healthcare services. To allow for this sharing of duties, HIPAA rules require that a written agreement be in place between the covered entity and the business associate. This agreement clearly defines the duties of the parties that are to be performed under the contract as well as obligations imposed on both the parties as required under HIPAA/HITECH laws.

For context, the definitions of both a covered entity and a business associate are defined in 45 CFR 160.103, which is cited herein and incorporated by reference.

While the above example references parties such as a covered entity and a business associate with respect to HIPAA/HITECH obligations, the present technology can apply any contractual provision that imposes obligations on a party to the contract in the event of a data incident.

In one embodiment, a covered entity could include a hospital group that services patients. A business associate of the hospital group could include a billing and accounting service that has access to patient information. The accounting service provides a business function to the hospital and encounters potential or actual PII or PHI. A service agreement is established between the hospital group and the accounting service and this agreement includes several provisions that deal with how PII and PHI are to be maintained by the accounting service. The service agreement also includes notification obligations that specify how the accounting service should handle notifications to the covered entity or patients in response to a data incident.

In another embodiment, a doctor's group which operates out of the hospital would be considered a covered entity with respect to its patients. The hospital group would be a business associate of the doctor's group that uses the hospital facilities.

The obligations found in a service agreement can be manually into the risk assessment server by one or more parties. In another embodiment, the service agreement can be uploaded to the risk assessment server and the risk assessment server can extract relevant obligations from the service agreement relating to data incident obligations. Additionally, an identification of a role for each party to the agreement can be made. In this, the risk assessment sever can efficiently identify notification obligations for a party to the service agreement and create notification schedule that includes the relevant contractual notification obligations, as well as other state and federal notification obligations imposed by statute.

Using the examples above, it will be appreciated that an entity can be both a covered entity and a business associate, but these roles depend on the natural of the relationship with the entity and other entities, defined by a contractual relationship.

The suggestions or recommendations generated by the risk assessment server are dictated, in some embodiments, by the role assumed by a party to a contractual agreement. Because a party can be both a data owner (covered entity) and a data maintainer (business associate), relative to the same data incident.

For example, generating a notification schedule can include generating a first notification schedule for a party when the party is acting as a data owner and generating a second notification schedule for the party when the party is acting as a data maintainer. To be sure, the creation of the first and second notification schedules occurs in response to the same data incident.

The extraction of obligations can include the risk assessment server analyzing the service agreement for keywords or phrases indicative of notification obligations.

Figure 16:
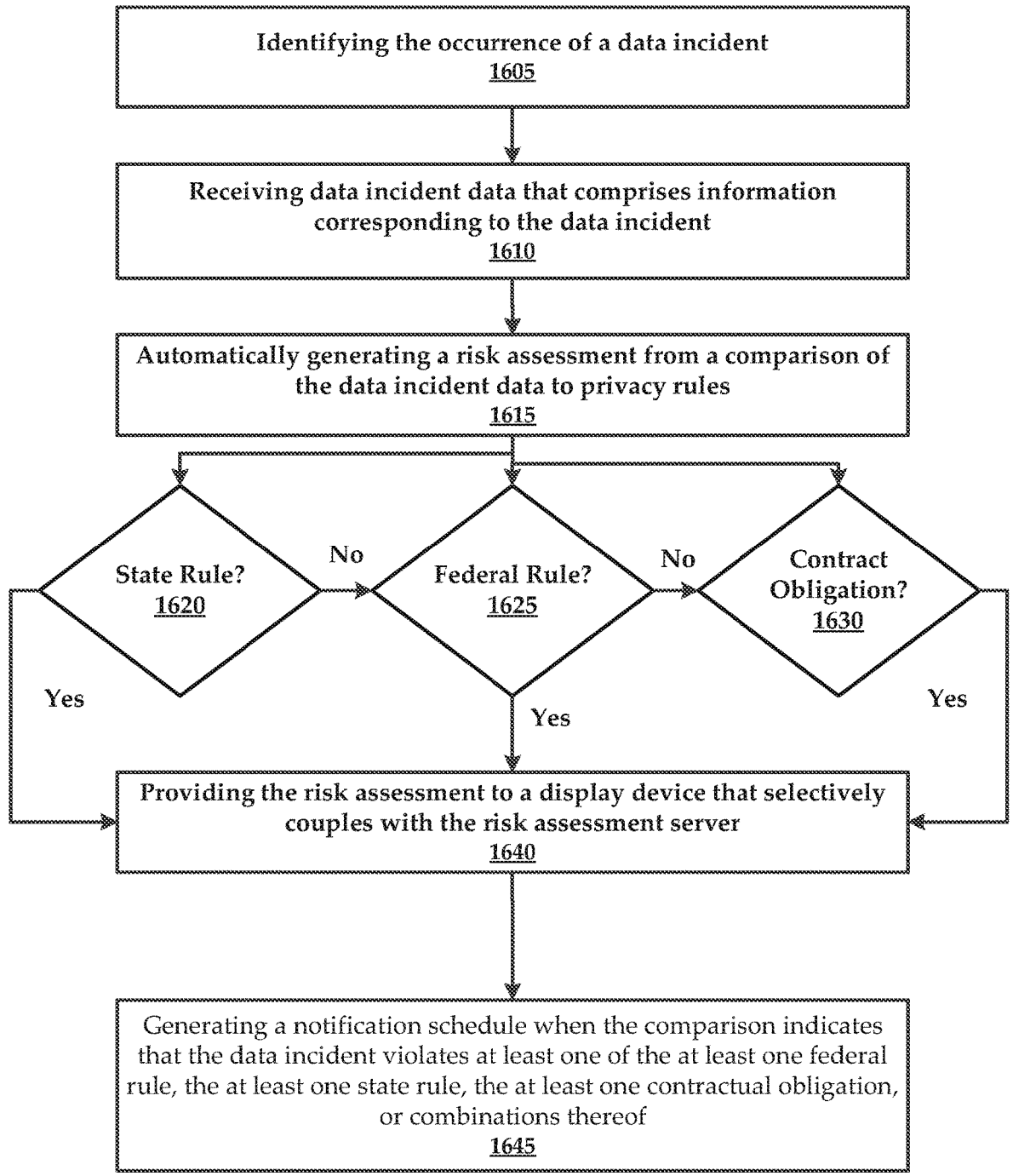
FIG. 16 is a flowchart of a method for managing a data incident, the method including at least one contractual obligation.

FIG. 16 is a flowchart of an example method that is executed in accordance with the present technology. The risk assessment server described above can be configured to execute the method illustrated in FIG. 16.

In some embodiments, the method includes identifying 1605 the occurrence of a data incident. Once a data incident has been identified, the method includes receiving 1610 data incident data that comprises information corresponding to the data incident. The data incident data can comprise, for example, the identities of the parties involved in the data breach/incident.

As mentioned above, the data incident is defined by the intentional or unintentional release of personally identifiable information to an untrusted environment.

Next, the method includes automatically generating 1615 a risk assessment from a comparison of the data incident data to privacy rules. In one embodiment, the method includes determining 1620 if at least one federal rule should be applied. Also, the method includes determining 1625 if at least one state rule should be applied.

To be sure, each of the state and federal rules define requirements associated with data incident notification laws.

In some embodiments, the method includes determining 1630 if at least one contractual obligation defining contractual requirements of a breaching party due to the data incident. As mentioned previously, the breaching party is a party to the at least one contractual obligation, such as a covered entity and a business associate.

The method also comprises providing 1640 the risk assessment to a display device that selectively couples with the risk assessment server, as well as generating 1645 a notification schedule when the comparison indicates that the data incident violates at least one of the at least one federal rule, the at least one state rule, the at least one contractual obligation, or combinations thereof.

The method described above can be executed in any order. Steps can be added, omitted, and/or modified as required so long as the steps selected for the method are consistent with the teachings provided herein. For example, the method can include a step of determining a role for each entity in a contractual agreement. This process can occur before the data incident occurs or can be performed after the data incident occurs, but prior to creation of the notification schedules.

Figure 17:
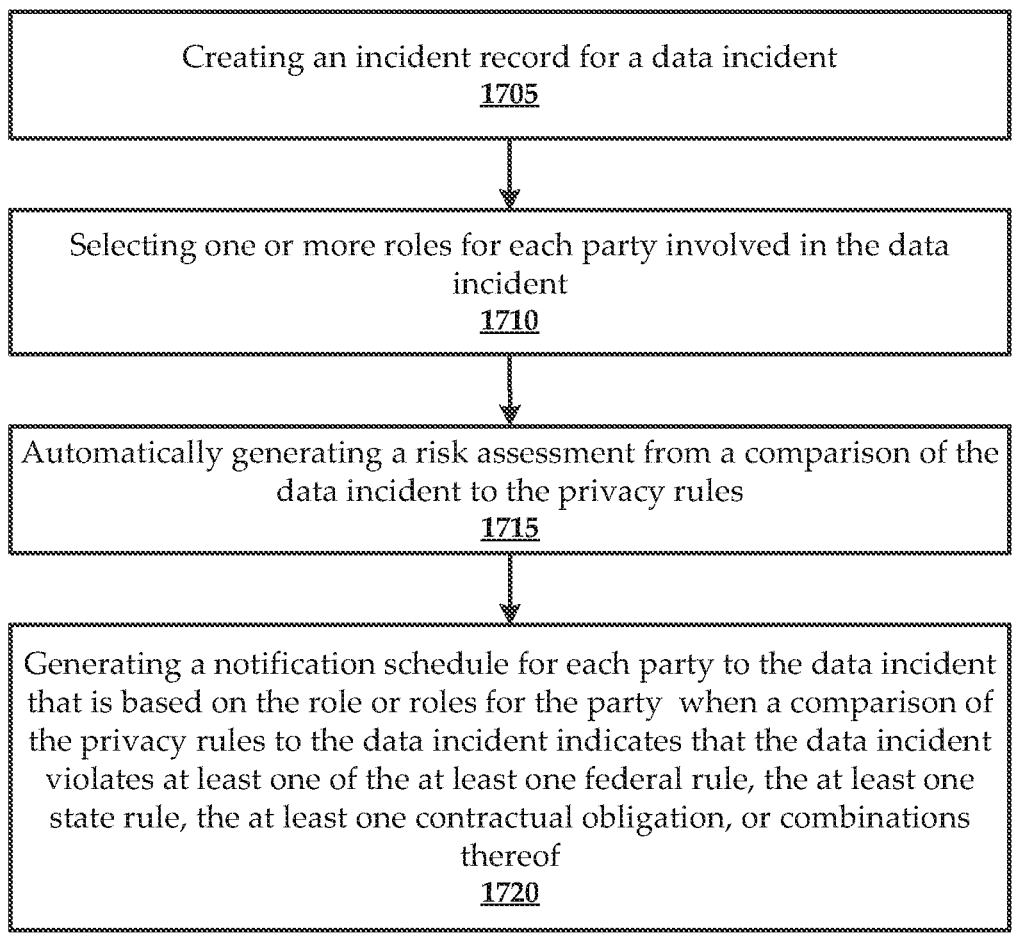
FIG. 17 is a flowchart of a method for managing a data incident involving parties with different roles.

FIG. 17 is a flowchart of a method for managing a data incident.

As with the method of FIG. 16, the risk assessment server is utilized to perform the method. Generally, the method of FIG. 17 involves the identification of a data incident and the selection of a role for a party that is based on a contractual agreement between that party and one or more parties. The role, in part, dictates the obligations imposed on that party either by state or federal law, as well as any obligations for that party set forth in the agreement. For context, some state and federal laws impose duties or obligations on a party depending upon whether they are a data owner or a data maintainer. By way of example, HIPAA laws impose duties on both covered entities and business associates. These obligations are different for each role. As mentioned above, a party can be both a covered entity and a business associate within the context of a single data breach.

The method includes a step of creating 1705 an incident record for a data incident. This data record includes information regarding the data incident.

Next, the method includes selecting 1710 one or more roles for each party involved in the data incident. Again, a single party can be assigned two or more roles for a single incident.

Once the incident has been identified and one or more roles assigned to each party to the data incident, the method includes automatically generating 1715 a risk assessment from a comparison of the data incident to the privacy rules.

The method also includes generating 1720 a notification schedule for each party to the data incident that is based on the role or roles for the party when a comparison of the privacy rules to the data incident indicates that the data incident violates at least one of the at least one federal rule, the at least one state rule, the at least one contractual obligation, or combinations thereof.

In some embodiments, the present technology can leverage an external entity workflow to manage complex relationships and obligations between contracting parties. Thus, in addition to having regulatory obligation imposed by regulatory agencies who apply state and federal privacy rules, parties can also have specific notice obligations that stem from contractual obligations between parties.

Specific definitions and descriptions for various parties are provided for clarity of description. On type of party is a covered entity (CE), which comprises an entity that is covered by federal or state privacy laws, some of which require notification obligations to impacted parties. According to the HHS (health and human services) definition, a CE can be a Healthcare Provider such as a doctor or healthcare clinic, a Health Plan (e.g., health insurance company, HMO, Medicare/Medicaid), or a Healthcare Clearing House. According to the FTC (federal trade commission), a CE is a financial institution.

Another type of party is a Business Associate/Service Provider. According to the HHS definition, a business associate (BA) is a person or entity that creates, receives, maintains, or transmits protected health information to perform certain functions or activities on behalf of a covered entity. The equivalent entity in the financial world is referred to as a Service Provider (SP).

Parties can enter into a Business Associate Agreement (BAA), where the BAA is the contract between a CE and an external entity that covers obligations such as notifications, indemnification, and so forth.

In some instances, these BAAs (as well as other contracts) can include indemnification clauses. If there is a data breach or HIPAA violation, these events can incur costs such as attorney fees, notification costs, credit monitoring, or fines. An indemnification clause determines who pays the costs. If you are the indemnified party, an indemnification clause is a promise by the other party to cover your losses if they do something that causes you harm. "Indemnify" and "hold harmless" mean the same thing—to make whole after causing a loss. See article on HIPAA.com.

A subcontractor is a person or entity to which a business associate delegates a function, activity or service in a capacity other than as a member of the workforce of such business associate.

An upstream/downstream position describes where an entity exists in the chain of HIPAA or FTC compliance. For example, a BA is downstream of a CE, a subcontractor is downstream of a BA, and a CE is upstream from a BA and a subcontractor—just to name a few.

An external entity is an organization with which a first party has a relationship as defined by a contract. The relationship can be as a client, business associate, service provider, or subcontractor.

In some instances, parties can implement a fully insured or self-funded health plan. Employers that offer health insurance benefits finance those benefits in one of two ways: (1) they purchase health insurance from an insurance company (fully insured plans), or they self-fund the health benefits directly for employees (self-funded or employee sponsored plans) and contract with insurance companies to serve as third-party administrators of the insurance plan. Employers with self-funded plans are usually considered to be CE's and must comply with the HIPAA privacy and security rules. This is because the employer has access to its employees' medical information, either directly or through a third-party administrator (TPA). Usually, the TPA is a health insurance company.

In general, the external workflow processes described herein can support covered entities as defined by HIPAA and their obligations under HIPAA Final Rule, and financial institutions as defined by the FTC and their obligations under GLBA. The external entities workflow extends the functionality of the risk assessment server (described in greater detail infra) to include external entities (BA or SP) that have obligations to clients, individuals, and agencies. The risk assessment server can be configured to handle contractual obligations similarly to regulatory jurisdictions.

The risk assessment server can implement various UIs to request, capture, process, and identify notification obligations for contracting parties. In some embodiments, the risk assessment server can create external entities, define contacts and notifications, and define notification rules.

The risk assessment server can configure specific properties to "unlock" the external entities workflow. For example, the risk assessment server can set properties that trigger notice obligations. When the properties of a data incident match these triggers, a party is informed that their notice obligations have been triggered. This informational process can specify entities requiring notification, the content of the required notification, and so forth.

In some embodiments, the risk assessment server can specify one or more affected external entities, and at least one regulatory jurisdiction involved in the data incident.

An assessment of the incident can occur and can be conducted in accordance with any of the embodiments described above.

According to some embodiments, the risk assessment server can optionally generate and/or display various UIs that allow a party to view the regulatory assessment results and evaluate whether any jurisdictions are notifiable breaches.

In some embodiments, an example workflow can comprise a covered entity creating a data incident record within the risk assessment server. The CE can initiate a workflow on its own behalf in this embodiment. The CE defines a source, which is itself as well as its role as a CE. The CE can select employees who were involved in the data incident. In another embodiment the CE can create a workflow for an incident on behalf of a BA. In these embodiments, the CE can specify that the source is external in nature (a BA) and that the reporting party is a CE. The risk assessment server then specifies the name of the BA who caused the incident and may also specify an incident date. The CE can utilize the risk assessment server to determine its notice obligations, if any and begin the notification and remediation process. The CE can utilize the risk assessment server to monitor the implicated BA's compliance to its contractual notice obligations.

In another example data incident, a BA causes a breach that has impacted one or more CEs and the BA can be obligated due to contractual obligations with CEs. In this example, the BA can create the incident report and define any relevant properties such as role, employees, and so forth.

A BA can also specify a data incident on behalf of a subcontractor. Again, the subcontractor is a downstream entity of a BA. When the subcontractor reports the incident to the BA, the BA can define incident properties such as source, role, employee(s), BA, and informed date (e.g., the date on which the BA was informed by the subcontractor that a data incident had occurred).

In some embodiments, a notifying party can be defined as a hybrid entity that has both regulatory and external entity obligations. In these instances, the party can be obligated due to a state law, a federal law, and/or a contractual obligation.

FIG. 18 illustrates a table that includes a list of entity designations, roles, and permutations of internal and external notification obligations based on party type and an associated role.

Figure 19:
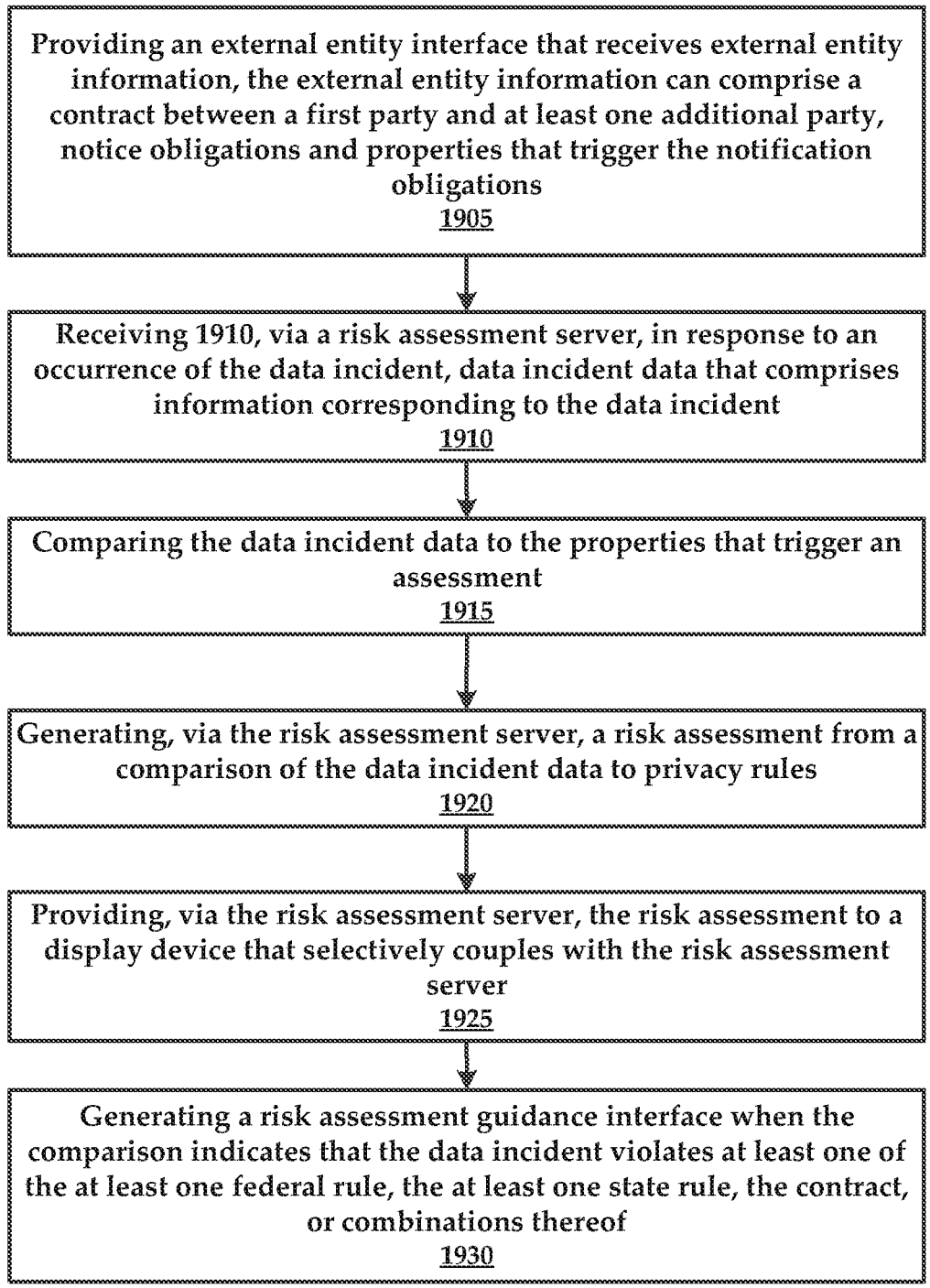
FIG. 19 is a flowchart of a method for external entity workflow for a data incident.

FIG. 19 is a flowchart of an example method of an external workflow process. As with the methods above, the risk assessment server is utilized to perform the method. In some embodiments, the method comprises the risk assessment server providing 1905 an external entity interface that receives external entity information. In some embodiments, the external entity information can comprise a contract between a first party and at least one additional party. For example, one of the parties can upload a copy of a contract between the first party and at least one additional party. This contract specifies contract clauses that can include notification obligations, such as the indemnification agreement/clauses defined above. The contractual obligations can take various forms as would be appreciated by one of ordinary skill in the art.

In some embodiments, a party can define notification obligations that specify when the first party or the at least one additional party notifies entities that a data incident has occurred, as well as properties that trigger an assessment of the notification obligations.

The properties can include many permutations of various quantities/qualities/parties. These properties can include source (either internal or external), party role, breaching party relationship, incident date, and incident details.

In some embodiments, some properties that can affect the assessment, or can be deleted or deactivated such as a Relationship Contractual Notify Rule, a Regulatory Notify Rule, Timeline, Contacts, Notifications, and Active/Resolved. Changes can be saved in the UI at any time. The changes will propagate to existing incidents as described (and configured) in the Message column. The server may not allow locked incidents to be updated because of a desire to maintain the integrity of the assessment history.

Deleting a contact or notification or deactivating an external entity removes the relevant configuration from the server. If changes are applied to incidents that are assessed but unlocked, the assessment data is cleared and users must reassess the incident. A new contact can be created at any time without risk.

Properties that are displayed in the incident but don't affect the assessment include, but are not limited to Entity Name, Entity Type, Contact Name, Notification Name, Notification Method, and Notification Summary.

In some embodiments, the method can comprise receiving 1910, via a risk assessment server, in response to an occurrence of the data incident. The data incident data comprises information corresponding to the data incident, the data incident further comprising intentional or unintentional release of personally identifiable information to an untrusted environment by the first party or the at least one additional party.

Next, the method includes comparing 1915 the data incident data to the properties that trigger an assessment. To be sure, if the properties indicate that an assessment is required the method further comprises generating 1920, via the risk assessment server, a risk assessment from a comparison of the data incident data to privacy rules.

In some embodiments, the privacy rules comprise one or more of the following: (a) at least one federal rule; (b) at least one state rule, each of the rules defining requirements associated with data incident notification laws; and (c) the contract.

According to some embodiments, the method includes the providing 1925, via the risk assessment server, the risk assessment to a display device that selectively couples with the risk assessment server.

Additionally, the method includes generating 1930 a risk assessment guidance interface when the comparison indicates that the data incident violates at least one of the at least one federal rule, the at least one state rule, the contract, or combinations thereof.

FIG. 20 is an example risk assessment guidance interface 2000. The interface 2000 comprises a basic information section 2002 that defines various entity or party data. The interface 2000 also comprises a contract upload mechanism 2004 that allows one or more parties to upload a contract that defines the notification obligations between the parties.

In some embodiments, the interface 2000 can also comprise a notifications section 2006 that allows a party to specify notification obligations. In some instances, default notification obligations can be implemented if no specific notification obligations are defined.

To be sure, the properties that trigger the notification obligations can be determined from the party information collected in section 2002, as well as the contractual information uploaded in section 2004.

Figure 21:
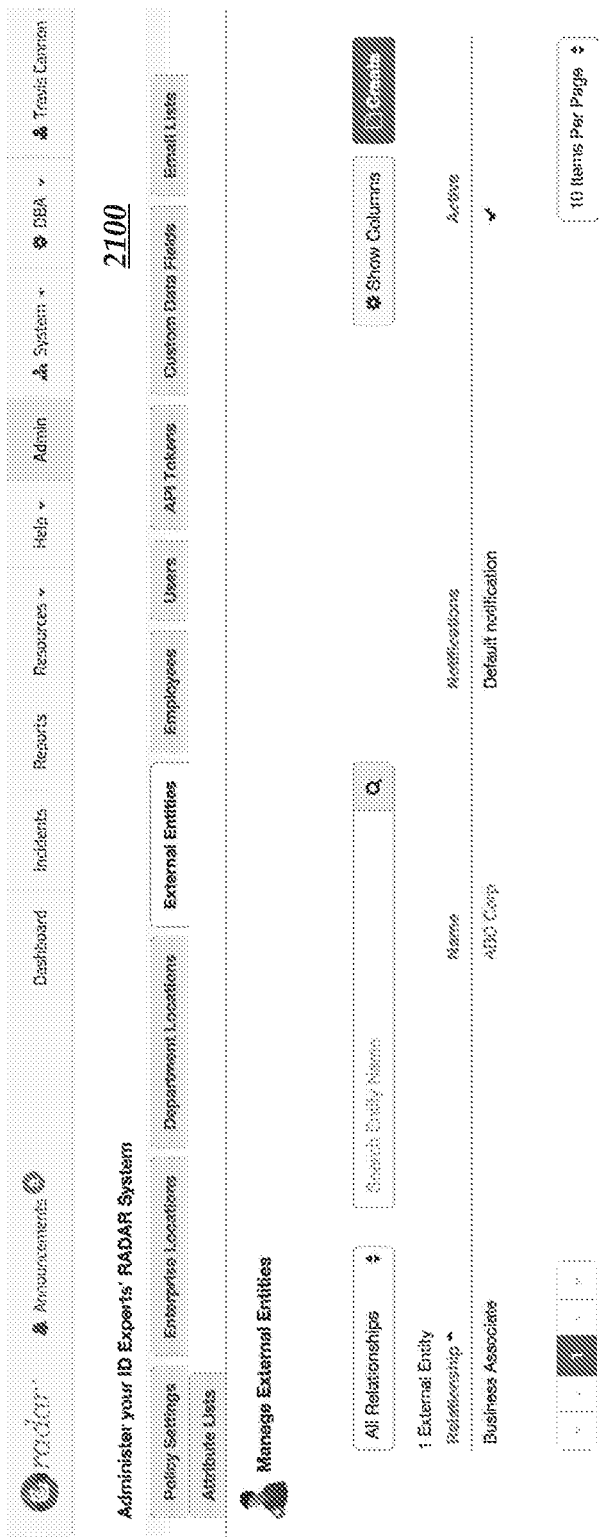
FIG. 21 is a graphical user interface that provides a list of external entities.

FIG. 21 illustrates another example risk assessment guidance interface 2100 that allows a party to manage its external entity relationships. For example a business associate ABC Corp is listed. Each of the entities defined using the assessment interface 2000 of FIG. 20 will be listed in the interface 2100.

Figure 22:
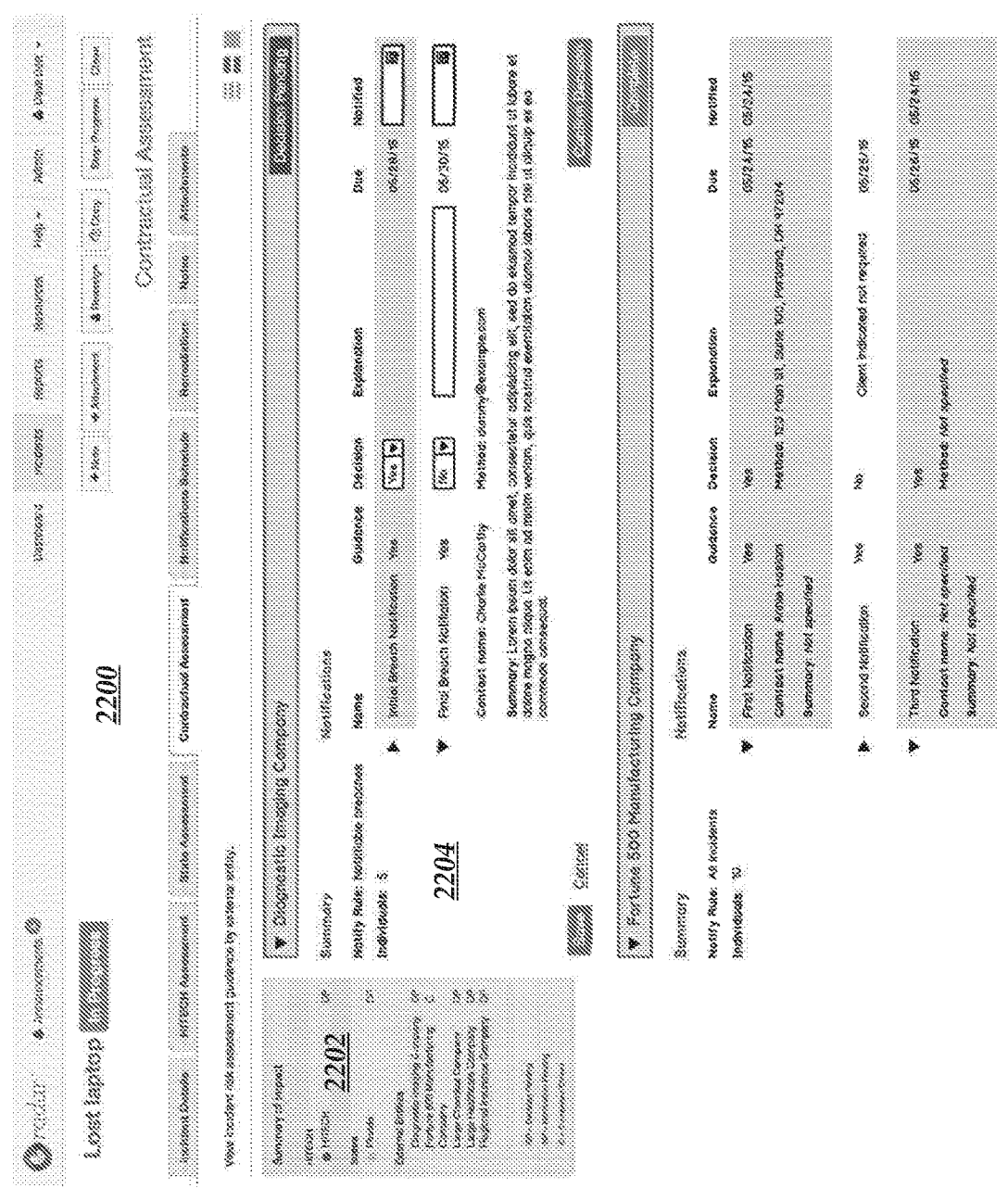

FIG. 22 is a screenshot of a detailed incident assessment user interface 2200. Specifically, this UI 2200 includes a contract based assessment of obligations. A summary section 2202 is provided which indicates violation type, which in this instance includes HIPAA HITECH (federal rule). The summary section can also identify impacted external entities and status of analysis for each of the external entities.

A breach assessment section 2204 provides the specific details of an identified data incident, for two specific entities/parties. The first entity is a diagnostic imaging company and the second entity is a fortune 500 manufacturing company. To be sure, these entities are the parties to which a BA or other downstream external entities are obligated to notify that a privacy incident has occurred. Each of these entities will have a detailed summary about whether they have been or will be notified and status indicator for the current notification analysis.

Figure 23:
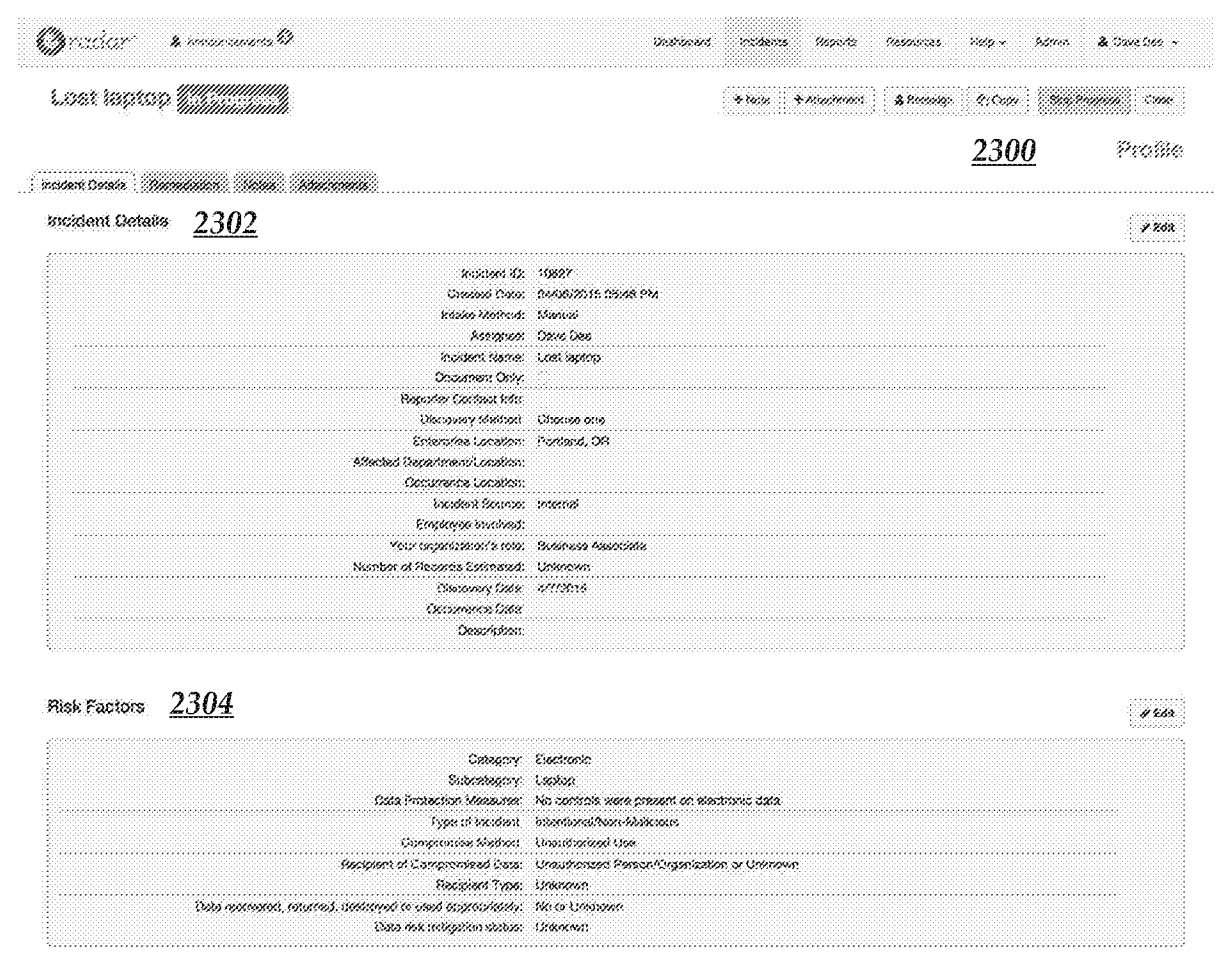

FIG. 23 includes a detailed incident interface 2300 that provides a robust set of details for an identified incident. An incident detail section 2302 includes attributes of the incident gathered from the incident details provided by a reporting party. A risk factor section 2304 is also included that provides more specific details regarding the severity of the data incident.

Figure 24:
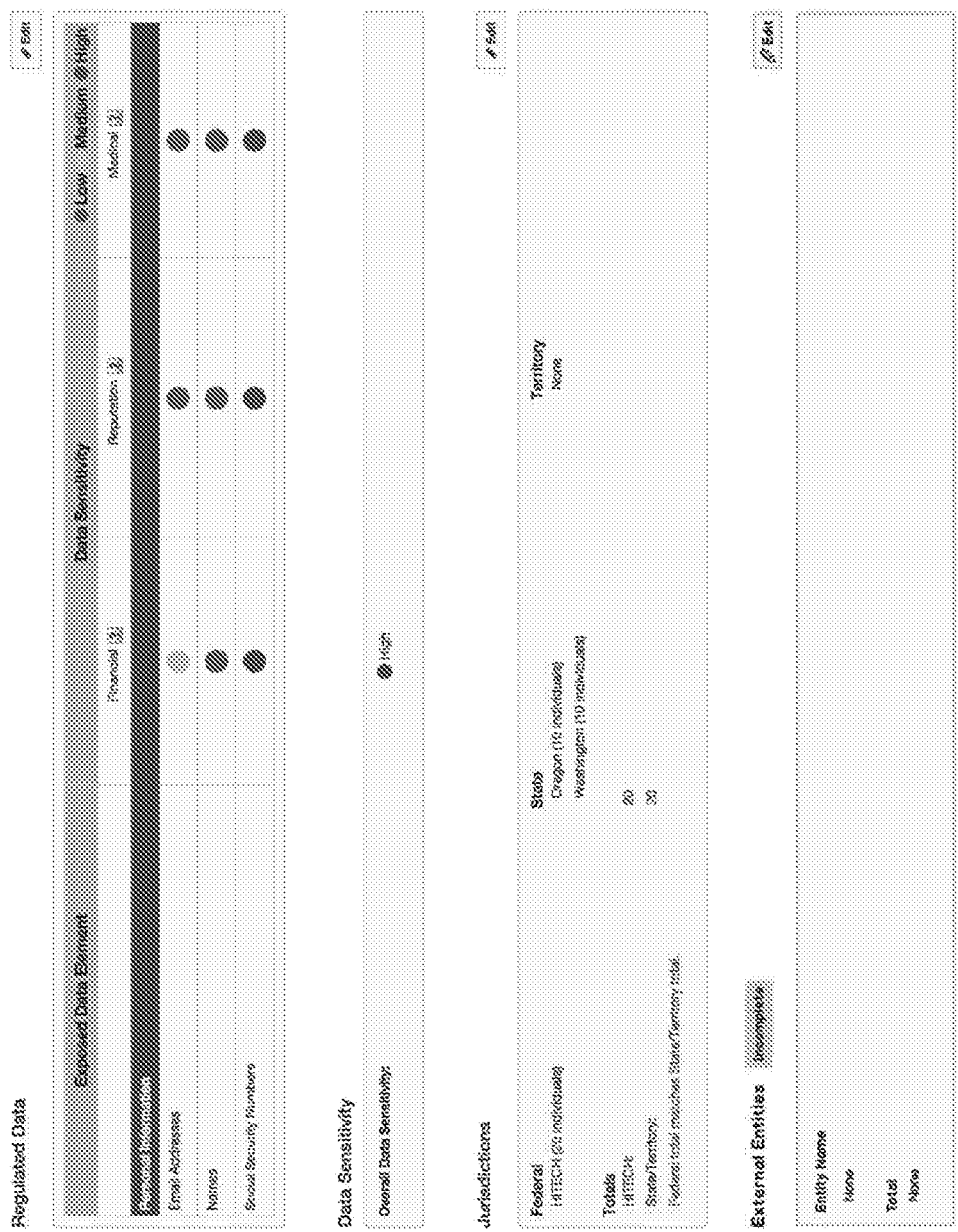
FIG. 24 is a graphical user interface that provides yet additional details regarding the data incident in addition to those provided in FIG. 23.

FIG. 24 is another summary interface 2400 that includes various sections that provide additional details regarding a data incident. The interface comprises a regulated data section 2402, a data sensitivity section 2406, a jurisdictions section 2408, and an external entities section 2410. These various sections can include visual indicators that inform a user as to the types of data involved in the data incident, as well as a sensitivity level of the data involved in the incident, as well as any jurisdictions involved (e.g., if state or federal rules are implicated), and a list of any external entities that are involved in or impacted by the data incident.

FIGS. 25-26 illustrate a table of external entity administration console features. FIGS. 27-33 illustrate a table of external entity workflow features for the risk assessment server. Some of the illustrated features require customer licensing. FIGS. 34-35 collectively illustrate a table of additional functionalities that can be implemented by the risk assessment server. These features illustrated in FIGS. 25-35 are not intended to be limiting in any way but are example features and logic that can be implemented by the risk assessment server.

Multifaceted Analyses

According to some embodiments, the methods described herein can be extended to include aspects of multi-faceted analyses of data incidents. For context, an incident can have multiple facets. In one example, a data incident can comprise a situation such as a stolen briefcase containing regulated data (PII/PHI, personal data) across multiple categories (paper, electronic) and having different data protection measures. This data incident can include unauthorized disclosure of regulated data for US- and EU-based employees. Each of these aspects or facets increases the complexity of any analysis performed. Furthermore, each of the facets can trigger different sets of notification obligations.

It will be understood that regardless of how many facets a privacy incident may include or comprise, the facets are collectively managed as a single incident. While specific facets can be analyzed independently of one another, a multifaceted privacy incident is considered an integrated unit.

Protected data or privacy data, as referred to herein, can include any data that, if disseminated in an unauthorized manner, would violate one or more privacy rules, such as governmental, non-governmental, and/or contractual rules, obligations, provisions and similar contractual components. Violation of these rules would result in the triggering of notification obligations and/or other remediating measures in order to mitigate or compensate for the unauthorized dissemination of privacy data. Examples include, but are not limited to, personally identifiable information, and personal health information for instance related to governmental rules. Other types of privacy data could include confidential information, trade secrets, IP, or other contractually protected information.

In some embodiments, a facet comprises a collection of various types of privacy data. Examples of privacy data include any combination of risk factors, data elements, jurisdictions, and so forth, or any combinations thereof. In one or more embodiments, each incident region (e.g., US or EU, G.D.P.R., Canada PIPEDA) comprises one or more facets where the incident region determines which laws apply to the facets. These laws are referred to herein in some instances as a regulatory framework.

In some embodiments, each facet may have one or more privacy rules that are implicated. For example, a facet involving a loss of paper documents may involve both a state privacy rule and a federal privacy rule. In other instances, a facet may involve only a single privacy rule. Again, some privacy rules can be determined from relevant regulatory framework(s) that are implicated by the specific data incident(s) involved. Those privacy rules can be defined contractually between two or more parties.

Some embodiments of facets also have a collection of privacy data, which is determined by the regulatory region or regulatory body. In various embodiments, each facet can also be assessed independently of other facets. Again, some facets may not be associated with a regulatory region or regulatory agency.

In order to assess an incident with multiple facets, at least one facet comprises a completed set of privacy data. A number of overlapping (non-unique) individuals is specified across all facets associated with a jurisdiction so that the system can determine if agency notification thresholds have been exceeded.

While some embodiments consider privacy incidents and obligations relative to laws, a privacy rule need not relate to governmental regulations or statutes. In some embodiments, a privacy rule could include a non-governmental regulatory body, such as a voluntary privacy organization that certifies entities and their practices. In another example, privacy rules can comprise inter-party contractual obligations. For example, one party can contract with a second party that one or more of the parties are to hold certain information confidential. The contract can specify what notification or remediation obligations exist with regard to breaches with respect to this contractually defined confidential information. The present disclosure can be utilized in any of these (or combinations of these) scenarios.

In one example use case, the following information will be assumed as known. For example, the privacy incident can include a stolen briefcase containing: (1) Thumbdrive—The encryption key and password were compromised; (2) Tablet—No data protection measures were present; (3) Bank statements—The documents were redacted (i.e., an exception can be applied due to the redaction of the documents).

Additional aspects of the privacy incident include that only US regulatory or privacy rules are implicated (e.g., regulatory framework). These rules are governed by a regulatory agency such as the Federal Trade Commission. The regulatory frameworks provided by the FTC are thus relevant to the analysis. For purposes of explanation, it can be assumed that the incident also involves three specific State level jurisdictions such as CA, HI, OR, and paper exceptions (such as paper documents) apply in some cases. Each of these states may implement their own State-specific regulatory framework that will be consulted and evaluated relative to the data incident data of each facet.

Also, it is assumed that the user is subject to specific contractual notification obligations by virtue of an employment contract. For example, the owner of the briefcase signed an employment agreement that specified notification obligations to the employee's immediate superiors and the company's IT department. In this example, the employment contract imposes obligations on the employee to disclose any known or assumed data incidents within 12 hours. This obligation allows the company to quickly identify any governmental privacy rules that may apply to the data incident. Thus, the presence of a contractual obligation may be based, at least in part, on a privacy rule promulgated by an agency or government. In this example, a regulatory agency would include both a non-governmental agency or party such as the company or a privacy officer in the company, or a third party vendor in charge of privacy issues for the company. Another regulatory agency would include the government agencies that impose specific privacy rules on the unauthorized dissemination of contents in the stolen briefcase. Examples of governmental privacy rules and agencies will follow.

Private or contractual privacy obligations can include both notification obligations and/or mitigation and remediation obligations, as well as other similar duties. A mitigation or remediation obligation can specify, for example, that a breaching party is to immediately change all passwords or cease Enterprise systems usage for a period of time. For example, the employee can be prevented from accessing a corporate network until passwords or other security or authentication credentials have been reissued.

Further with this example, three specific facets can be identified across two major categories. For example, the first facet involves the thumbdrive, which has an electronic data type. A tablet also has an electronic data type, whereas the bank statements are a paper data type. While these facets are part of the analysis, one of ordinary skill in the art will recognize that these may not be the only ascertainable facets across this specific incident. Thus, this use case does not contemplate every possible facet-related workflow or configuration state, in order to preserve clarity and brevity of description.

Next, a basic workflow for the "stolen briefcase" incident is configured for three facets. In some embodiments, a facet operational mode is enabled. In this instance, a facet is represented as a browser-style tab on a Profile page. Each facet comprises a unique collection of privacy data (risk factors, data elements, and jurisdictions) displayed to the user. Next, a tab of the facet can be renamed by changing a default tab name to "Thumb drive."

Note that the user can choose a regulatory region (US, EU/G.D.P.R., State, etc.) and an organization's role (covered entity, business associate, etc.)

Other configurations that would be known to one of skill in the art can also be utilized. For example, any suitable regulatory regions and organizational roles can be included for selection by a user. In general, other facet specific configurations are selectable by the user to define, in greater or lesser detail, the attributes or parameters of their specific facets associated with the particular data incident(s) involved.

Next, the user can then select a category, which is electronic because the facet includes a thumbdrive. The user selects or defines a data protection measure that was breached, which indicates that an encryption key and password that were compromised.

Next, the user can select various data elements, and a summary of the selected data elements are displayed to the user. Next, the user then selects jurisdictions (if applicable) and specifies a number of individuals involved in the breach. Next, the system can then assess the facet. In some embodiments, the user can create a new facet by copying, in part or in whole, the privacy data of an existing facet.

According to some embodiments, the next facet is processed when the user specifies "Tablet" as a facet name and selects a privacy data to copy. The Tablet facet is created by the system. The user can edit the privacy data of this facet as needed.

In some embodiments, a "unique individuals" link appears when there are multiple facets. For example the unique individual's link can appear when a second or additional facet(s) are defined after a tab for the first facet has been created.

The user can click the "unique individuals" link to display the associated modal dialog. To be sure, the purpose of the dialog is to specify whether individuals overlap between facets for a jurisdiction. The dialog is organized by jurisdiction and includes associated facets and a number of individuals for each facet.

By default, the system treats all individuals as unique (i.e., no individuals overlap). Specifying a number of overlapping (non-unique) individuals allows the system to properly determine if agency notification thresholds are exceeded.

Next, the user can edit the risk factors. For example, for a category of electronic, the system can determine or receive a selection from a user that a data protection measure was not present. The user can then edit a number of individuals for each jurisdiction, which completes the tablet facet. To be sure, any number of facet tabs can be created for each facet of a multi-faceted data incident.

Both facets can be assessed by the system in tandem or sequentially. In some embodiments, the user can create a new facet from scratch, which involves the display of a new facet dialog UI. The user can then create a new facet that corresponds to the "Statements" referenced infra above as bank statements.

The Statements facet is created. To populate, the user completes the privacy data to assess this facet.

The user can then edit various categories, such as a category of "paper." Next, the user specifies that a data protection measure for the paper category is "redacted", where parts of the paper documents had been redacted.

The user then defines data elements, jurisdictions, and specifies a number of individuals involved with the Statements facet. Data elements clearly defined and corresponding jurisdictions are specified by the user. Per facet, the user can click a "unique individuals" link to display the associated modal dialog, where the "unique individuals" dialog has been updated with the new facet data. The user can then configure the dialog so that 50 individuals overlap in the Oregon jurisdiction for the two electronic facets.

In some embodiments, the user can choose to assess all three facets simultaneously. In this example California is considered. The three facets have a highest possible risk as indicated in a heat map (not shown).

An Affected Individuals section can be displayed to the user. This section can be expanded allowing the user to view results for each facet. Guidance for the electronic facets is "Yes", while the guidance for the paper facet is "No" because the Civil Code (defined in the particular regulatory framework applied) does not regulate paper.

The guidance for the attorney general is "No" because the notification threshold of 500 individuals has not been exceeded.

Table 1 of FIG. 36 illustrates a summary of a number of individuals specified for all jurisdictions across the three facets, and whether AG notification is required. It will be understood that notes about the AG notification threshold calculation include, California, where the California Civil Code applies, which does not regulate paper. Therefore, the paper facet does not contribute to the threshold calculation. The electronic facets results in 500 individuals implicated in the breach. This number of individuals does not exceed the notification threshold. Additionally, Hawaii regulates paper, but the redaction exception exists. Therefore, the paper facet does not contribute to the threshold calculation. The electronic facets results in 700 individuals, which does not exceed the notification threshold. Also, Oregon does not regulate paper. Therefore, the paper facet does not contribute to the threshold calculation. Adding the electronic facets indicates that in 300 individuals have been impacted, but this number is reduced to 250 since it is specified that 50 individuals overlap (are non-unique) across these two facets.

Figure 37:
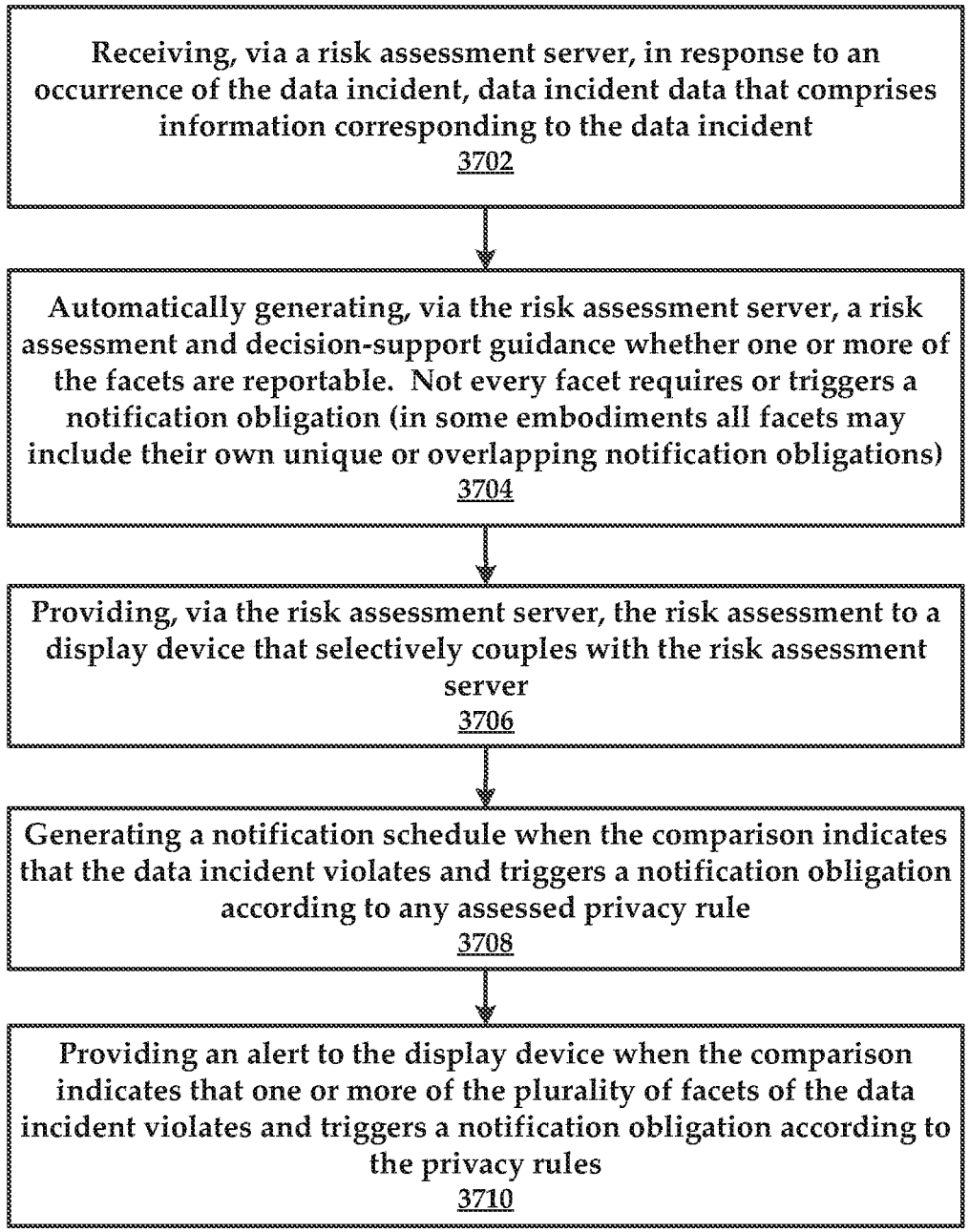
FIG. 37 is a flowchart of an example method for a multifaceted data incident of the present disclosure.

Using the embodiments and examples provided above, the present disclosure can be expressed through descriptions and illustrations of various example methods. For example, FIG. 37 illustrates an example method for managing a data incident. In this example, the data incident is a multi-faceted data incident. The method includes, for example, a step 3702 of receiving, via a risk assessment server, in response to an occurrence of the data incident, data incident data that comprises information corresponding to the data incident. In accordance with the embodiments disclosed throughout, the data incident further comprising intentional or unintentional compromise, disclosure or release of personal data or personally identifiable information to an untrusted or unauthorized environment.

It will be understood that the data incident comprises a plurality of facets, with each facet comprising any of unique and/or overlapping set of privacy data, media type (e.g., electronic or paper) and associated risk factors requiring facet specific incident risk assessment. The privacy data could include a thumbdrive and/or accounting documents in this example.

In some embodiments, the method includes a step 3704 of automatically generating, via the risk assessment server, a risk assessment and decision-support guidance that specifies whether one or more of the facets are reportable. To be sure, not every facet requires or triggers a notification obligation (in some embodiments all facets may include their own unique or overlapping notification obligations). This determination of potential reporting obligation(s) comes from a comparison of each of the facets to privacy rules.

As clearly noted above, the privacy rules can involve any combination of governmental rules, non-governmental rules, and/or contractual rules/obligations created between private parties.

To be clear, privacy rules that apply to at least a portion of the data facets can include reporting and/or remediation requirements associated with data incident notification obligations.

In some embodiments, the method comprises a step 3706 providing, via the risk assessment server, the risk assessment to a display device that selectively couples with the risk assessment server.

In general, the risk assessment comprises a risk level that indicates the severity of the data incident relative to the privacy rules. In some instances, the risk level is associated with a color. A hue of the color is associated with the severity of the data incident and a sensitivity of the data incident data as determined by the comparison.

In some embodiments, the risk assessment defines one or more exceptions that apply to at least a portion of the data incident data based upon the comparison. For example, an exception that includes a number of individuals having their privacy data breached is not sufficient to trigger a notification obligation, as provided in the examples above. In another example, an exception could include that a loss of paper documents is not a reportable incident.

According to some embodiments, a risk assessment comprises a determination as to whether a number of unique or non-unique individuals across the plurality of facets meet notification thresholds based on jurisdiction. For example, a number of individuals associated with data on the thumbdrive overlap with individuals identified in the accounting paperwork included in the briefcase. This is due to the fact that the thumbdrive includes backup electronic versions of the accounting paperwork that were also in the briefcase.

As noted above, each data incident and/or corresponding facet of the data incident could include risk factors, the data incident data, and a plurality of jurisdictions or regions (if governmental). Risk factors and data incident data are included in some embodiments. A risk factor can include one or more risks associated with dissemination of associated privacy data. Each facet can include its own type of privacy data and privacy rule(s).

In addition, one or more regulatory agencies may be implicated. For example, when the stolen briefcase includes information on both US and EU citizens, both US and EU regulatory agencies may need to be informed of the breach. Again, these agencies can be linked to the specific privacy rules associated with the privacy data and/or privacy rules implicated.

In some embodiments, one or more of the plurality of facets is capable of being assessed independently of other ones of the plurality of facets. For example, the dissemination of electronic privacy data from the loss of the thumbdrive can be evaluated independently of the dissemination of information through the loss of the paper documents in the briefcase. For example, if the privacy data on the thumbdrive happens to be different from that on the paper documents, the facets can be considered distinct from one another. For example, the thumbdrive could include resumes and/or employment contracts, while the paper documents included information relating to vendors for a company.

Thus, in some embodiments, each of the plurality of facets comprises a complete set of privacy data, as in the examples given above. These losses may be entirely orthogonal to one another, or may have at least some aspects of orthogonality or differentiation relative to one another.

In one or more embodiments, the privacy rules comprise at least one European General Data Privacy Regulation (G.D.P.R.) rule that governs privacy breaches relative to at least one of personal data, special categories of personal data, or combinations thereof. While G.D.P.R. has been disclosed, other similar governmental rules (e.g., framework) can be assessed in addition to G.D.P.R., based on the privacy rules implicated.

As noted above with respect to embodiments related to modeling of data, risk assessment methods can include modeling of the data incident data to the privacy rules to determine a severity and a data sensitivity of the data.

In another embodiment, the method can include modeling the data incident data to determine severity and data sensitivity of the data incident by evaluating the data incident data relative to the privacy rules, as well as generating a risk assessment from the modeling.

If the risk assessment indicates that a privacy rule has been violated, the method can include a step 3708 of generating a notification schedule when the comparison indicates that the data incident violates and triggers a notification obligation according to any assessed privacy rule.

In one or more embodiments, the method can comprise a step 3710 of providing an alert to the display device when the comparison indicates that one or more of the plurality of facets of the data incident violates and triggers a notification obligation according to the privacy rules. It will be understood that the notification schedule comprises notification dates that are based upon a violated one of the privacy rules, along with notification requirements that describe information that is to be provided to a regulatory agency or to an affected individual whose personal data has been compromised, disclosed or released as a result of the data incident.

Additional and optional method steps can include receiving information that is to be provided to a regulatory agency (could be governmental, non-governmental, and private) and storing the same in a content repository associated with the risk assessment server (or other system conducting the risk assessment).

Figure 38:
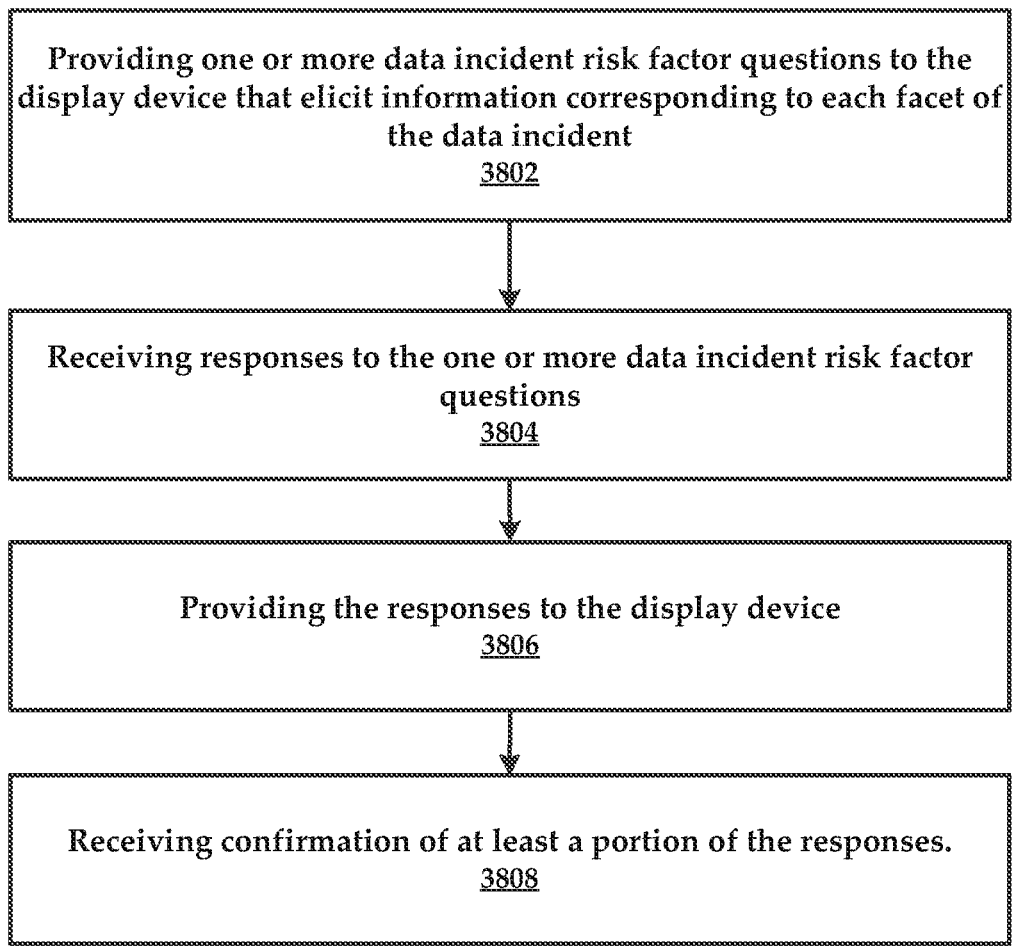
FIG. 38 is a flowchart of a related method for supporting a multifaceted data incident of the present disclosure.

FIG. 38 illustrates an example method for receiving data incident data in accordance with the present disclosure. The method can comprise a step 3802 of providing one or more data incident risk factor questions to the display device that elicit information corresponding to each facet of the data incident. Next, the method can comprise a step 3804 of receiving responses to the one or more data incident risk factor questions. Another step 3806 includes providing the responses to the display device, and then a step 3808 of receiving confirmation of at least a portion of the responses.

Multi-Region Data Incident Assessment.

Multi-Region Data Incident Assessment updates existing platforms to support a user interface and workflow that allows for selection of multiple regions in a data incident creation and investigation. Existing platforms are expanded for enhanced efficiency for incident response and investigation to cover global jurisdictions. In various embodiments Multi-Region Data Incident Assessment supports European General Data Privacy Regulation (GDPR).

In various embodiments the present technology assesses multiple regions separately including consolidate privacy data, consolidate Risk Factors (facet based) and cannot consolidate data elements (facet based). Additionally, multiple regional assessments are viewed independently per region, and region- and facet-specific fields. Multiple regional assessments may be based on when they are discovered/responsible party becomes aware—of the incident. Since For example, suppose one discovered a breach of US privacy data and then became aware of EU privacy data several days later. Multiple regional assessments may be optimization for later. For example, a user can still create a separate incident at the later discovery. Multiple regional assessments may estimate individuals since regions are separate (and can be assessed separately). For example, separate estimated individuals for each region. Multiple regional assessments may further have contextual sensitivity. For example, the context in which the sensitivity should be changed is region-based. Moreover, multiple regional assessments may group. Multiple regional assessments may include the group field regionalized since organizations will have different groups for different regions. Further, the user interface concerns for multiple regional assessments may include "Region selector that also supports other regions."

FIG. 39 illustrates a Table that includes profile data across configurations (intake and web form) for a multi-region data incident. FIG. 39 shows profile data across various configurations including one region, no facets 3900, one region, facets 3902, multiple regions, no facets 3904, multiple regions, facets 3906.

Figure 40:
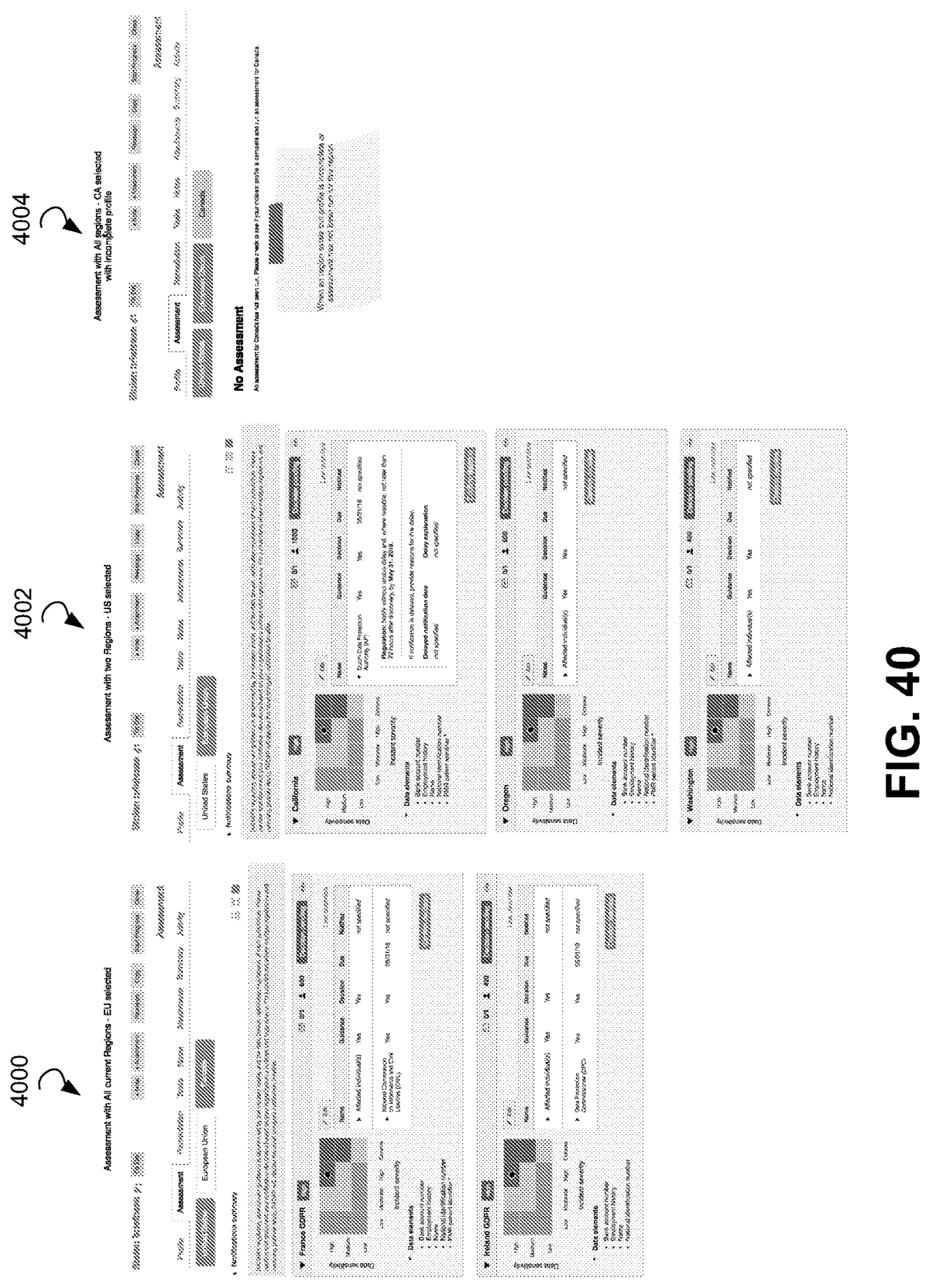

FIG. 40 is Graphical User Interfaces (GUIs) for an assessment of a multi-region data incident of the present disclosure. FIG. 40 shows selection of multiple regions with various jurisdictions for different data incident assessments. In various embodiments, if multiple jurisdictions are selected, the most stringent reporting requirements will be displayed. The European Union is selected in GUI 4000 with the France GDPR and Ireland GDPR. The United States is selected in GUI 4002 with California, Oregon and Washington selected. Canada is selected in GUI 4004 but a profile is not present for a specific jurisdiction.

Figure 41:
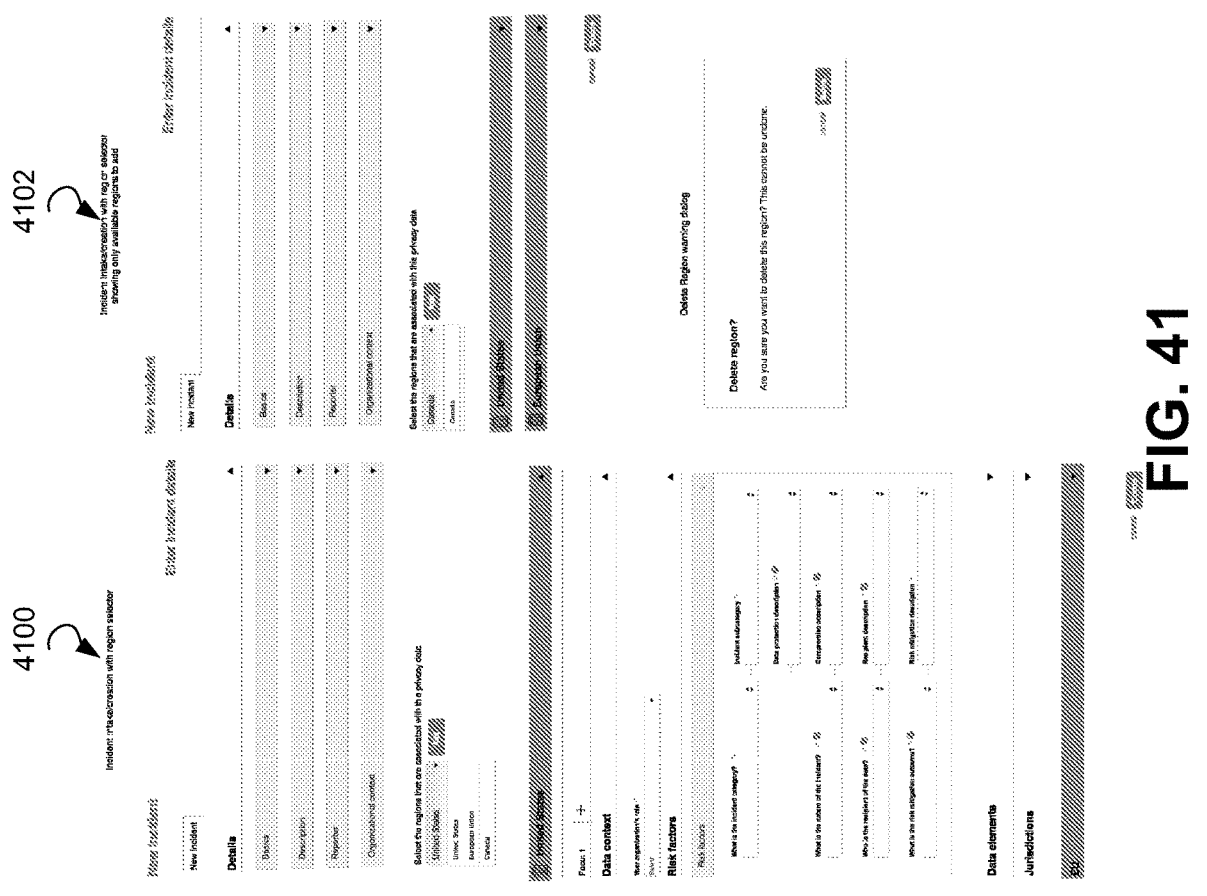
Figure 42:
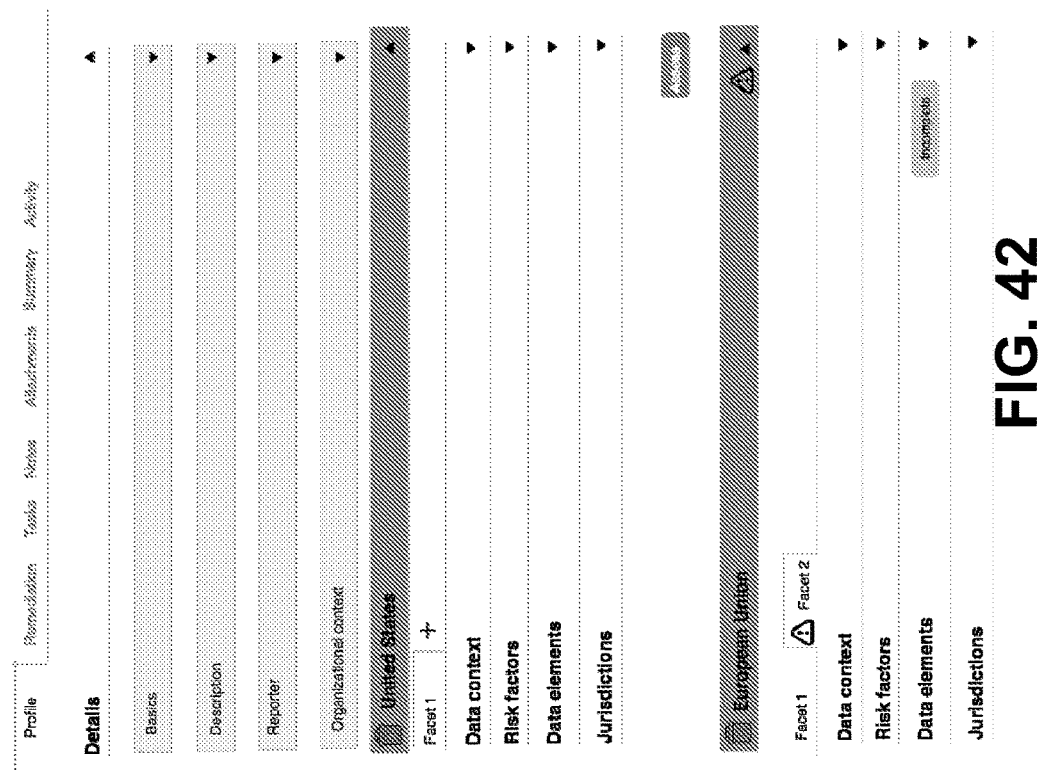
FIG. 42 is a Graphical User Interface (GUI) of a profile page for a multi-region data incident of the present disclosure.

FIG. 41 is Graphical User Interfaces (GUIs) of intake for a multi-region data incident of the present disclosure. FIG. 42 shows intake for a multi-region data incident with creation with a region selector shown in GUI 4100, and only available regions shown in GUI 4102.

FIG. 42 is a Graphical User Interface (GUI) of a profile page for a multi-region data incident of the present disclosure. A user is directed to a profile page 4200 for a region that is not currently available.

While various embodiments have been described above, it should be understood that they have been presented by way of example only, and not limitation. The descriptions are not intended to limit the scope of the technology to the particular forms set forth herein. Thus, the breadth and scope of a preferred embodiment should not be limited by any of the above-described exemplary embodiments. It should be understood that the above description is illustrative and not restrictive. To the contrary, the present descriptions are intended to cover such alternatives, modifications, and equivalents as may be included within the spirit and scope of the technology as defined by the appended claims and otherwise appreciated by one of ordinary skill in the art. The scope of the technology should, therefore, be determined not with reference to the above description, but instead should be determined with reference to the appended claims along with their full scope of equivalents.

What is claimed is:

1. A method for managing a data incident, comprising: receiving, via a risk assessment server, in response to an occurrence of a data incident, data incident data that comprises information corresponding to the data incident, the data incident further comprising intentional or unintentional release of personally identifiable information to an untrusted environment; automatically generating, via the risk assessment server, a risk assessment from a comparison of the data incident data to privacy rules, the privacy rules comprising at least one federal rule, each of the rules defining requirements associated with data incident notification laws; providing, via the risk assessment server, the risk assessment to a display device that selectively couples with the risk assessment server; wherein the receiving of the data incident data further comprises: providing, in response to a determination of at least one of the privacy rules, one or more questions to the display device that elicit information corresponding to the data incident, the one or more questions tailored to specific criteria of the at least one of the privacy rules; and receiving responses to the one or more questions; further comprising generating a notification schedule when the comparison indicates that the data incident violates and triggers a notification obligation according to the at least one federal rule; and wherein the notification schedule comprises notification dates that are based upon a violated federal rule, along with notification requirements that describe information that is to be provided to a regulatory agency or to an affected individual whose personal data has been compromised, disclosed or released as a result of the data incident.

2. The method according to claim 1, wherein the receiving data incident data comprises:
providing one or more questions to the display device that elicit information corresponding to the data incident;
receiving responses to the one or more questions;
providing the responses to the display device; and receiving confirmation of at least a portion of the responses.

3. The method according to claim 1, wherein the at least one federal rule comprises a federal statute that governs privacy breaches relative to at least one of protected health information (PHI), personally identifiable information (PII), or combinations thereof.

4. The method according to claim 1, wherein the risk assessment comprises a risk level that indicates a severity of the data incident relative to at least one of the at least one federal rule.

5. The method according to claim 4, wherein the risk level is associated with a color, wherein a hue of the color is associated with the severity of the data incident as determined by the comparison.

6. The method according to claim 1, wherein the risk assessment defines one or more exceptions that apply to at least a portion of the data incident data based upon the comparison.

7. The method according to claim 1, further comprising generating a notification schedule when the comparison indicates that the data incident violates at least one of the at least one federal rule.

8. The method according to claim 1, further comprising providing an alert to the display device when the comparison indicates that the data incident violates at least one of the at least one federal rule.

9. The method according to claim 7, wherein the notification schedule comprises notification dates that are based upon a violated statute, along with notification requirements that describe information that is to be provided to a regulatory agency.

10. The method according to claim 9, further comprising receiving the information that is to be provided to the regulatory agency and storing the same in a content repository associated with the risk assessment server.

11. The method according to claim 1, wherein the comparison includes modeling of the data incident data to the privacy rules to determine a severity and a data sensitivity of the data incident.

12. A method for managing a data incident, comprising: receiving, via a risk assessment server, in response to an occurrence of the data incident, data incident data that comprises information corresponding to the data incident, the data incident further comprising intentional or unintentional release of personally identifiable information to an untrusted environment; automatically generating, via the risk assessment server, a risk assessment from a comparison of the data incident data to privacy rules, the privacy rules comprising at least one federal rule, each of the rules defining requirements associated with data incident notification laws; providing, via the risk assessment server, the risk assessment to a display device that selectively couples with the risk assessment server; and further comprising generating a notification schedule when the comparison indicates that the data incident violates at least one of the at least one federal rule and when the comparison indicates that the data incident violates and triggers a notification obligation according to the at least one federal rule; wherein the notification schedule comprises notification dates that are based upon a violated federal rule, along with notification requirements that describe information that is to be provided to a regulatory agency or to an affected individual whose personal data has been compromised, disclosed or released as a result of the data incident.

13. The method according to claim 12, wherein receiving data incident data comprises:

providing one or more questions to the display device that elicit information corresponding to the data incident;
receiving responses to the one or more questions;
providing the responses to the display device; and
receiving confirmation of at least a portion of the responses.

14. The method according to claim 12, wherein the at least one federal rule comprises a federal statute that governs privacy breaches relative to at least one of protected health information (PHI), personally identifiable information (PII), or combinations thereof.

15. A method for managing a data incident, comprising: receiving, via a risk assessment server, in response to an occurrence of the data incident, data incident data that comprises information corresponding to the data incident, the data incident further comprising intentional or unintentional release of personally identifiable information to an untrusted environment; automatically generating, via the risk assessment server, a risk assessment from a comparison of the data incident data to privacy rules, the privacy rules comprising: at least one federal rule, each of the rules defining requirements associated with data incident notification laws; and at least one contractual obligation defining contractual requirements of a breaching party due to the data incident, the breaching party being a party to the at least one contractual obligation; providing, via the risk assessment server, the risk assessment to a display device that selectively couples with the risk assessment server; and generating a notification schedule when the comparison indicates that the data incident violates at least one of the at least one federal rule, the at least one contractual obligation, or combinations thereof and wherein the notification schedule comprises notification dates that are based upon a violated federal rule or a violated contractual rule, along with notification requirements that describe information that is to be provided to a regulatory agency or to an affected individual whose personal data has been compromised, disclosed or released as a result of the data incident.

16. The method according to claim 15, wherein receiving data incident data comprises:

providing one or more questions to the display device that elicit information corresponding to the data incident;
receiving responses to the one or more questions;
providing the responses to the display device; and
receiving confirmation of at least a portion of the responses.

17. The method according to claim 15, wherein the at least one federal rule comprises a federal statute that governs privacy breaches relative to at least one of protected health information (PHI), personally identifiable information (PII), or combinations thereof.

18. A method for managing a data incident, comprising: providing an external entity interface that receives: external entity information comprising: a contract between a first party and at least one additional party; notification obligations that specify when the first party or the at least one additional party notifies entities that a data incident has occurred; and properties that trigger an assessment of the notification obligations; receiving, via a risk assessment server, in response to an occurrence of the data incident, data incident data that comprises information corresponding to the data incident, the data incident further comprising intentional or unintentional release of personally identifiable information to an untrusted environment by the first party or the at least one additional party; comparing the data incident data to the properties that trigger an assessment; wherein if the properties indicate that an assessment is required, generating, via the risk assessment server, a risk assessment from a comparison of the data incident data to privacy rules, the privacy rules comprising: at least one federal rule, each of the rules defining requirements associated with data incident notification laws; and the contract; providing, via the risk assessment server, the risk assessment to a display device that selectively couples with the risk assessment server; generating a risk assessment guidance interface when the comparison indicates that the data incident violates at least one of the at least one federal rule, the contract, or combinations thereof; wherein the risk assessment guidance interface comprises an impact summary that indicates which federal rule was violated and one or more external entities implicated or impacted in the data incident; and further comprising generating a notification schedule when the comparison indicates that the data incident violates and triggers a notification obligation according to the at least one federal rule or a contractual rule; wherein the notification schedule comprises notification dates that are based upon a violated federal rule or a contractual rule, along with notification requirements that describe information that is to be provided to a regulatory agency or to an affected individual whose personal data has been compromised, disclosed or released as a result of the data incident.

19. The method according to claim 18, wherein receiving data incident data comprises:
providing one or more questions to the display device that elicit information corresponding to the data incident;
receiving responses to the one or more questions;
providing the responses to the display device; and
receiving confirmation of at least a portion of the responses.

20. The method according to claim 18, wherein the at least one federal rule comprises a federal statute that governs privacy breaches relative to at least one of protected health information (PHI), personally identifiable information (PII), or combinations thereof.

* * * * *